(12) United States Patent
Panagiotou et al.

(10) Patent No.: US 11,191,723 B2
(45) Date of Patent: Dec. 7, 2021

(54) APPARATUS, SYSTEMS, AND METHODS FOR CONTINUOUS MANUFACTURING OF NANOMATERIALS AND HIGH PURITY CHEMICALS

(71) Applicant: Delphi Scientific, LLC, Maynard, MA (US)

(72) Inventors: Thomai Panagiotou, Winchester, MA (US); Robert Joseph Fisher, West Roxbury, MA (US)

(73) Assignee: Delphi Scientific, LLC, Maynard, MA (US)

(*) Notice: Subject to any disclaimer, the term of this patent is extended or adjusted under 35 U.S.C. 154(b) by 0 days.

(21) Appl. No.: 16/624,631

(22) PCT Filed: Jun. 24, 2019

(86) PCT No.: PCT/US2019/038705
§ 371 (c)(1),
(2) Date: Dec. 19, 2019

(87) PCT Pub. No.: WO2019/246615
PCT Pub. Date: Dec. 26, 2019

(65) Prior Publication Data
US 2020/0397696 A1    Dec. 24, 2020

Related U.S. Application Data

(60) Provisional application No. 62/788,298, filed on Jan. 4, 2019, provisional application No. 62/688,755, filed on Jun. 22, 2018.

(51) Int. Cl.
*B01F 5/00*    (2006.01)
*B01F 15/00*   (2006.01)
(Continued)

(52) U.S. Cl.
CPC ............ *A61K 9/1075* (2013.01); *A61K 31/05* (2013.01); *A61K 31/4545* (2013.01);
(Continued)

(58) Field of Classification Search
CPC .................................................. A61K 9/1075
See application file for complete search history.

(56) References Cited

U.S. PATENT DOCUMENTS 4,533,254 A    8/1985    Cook et al.
4,908,154 A    3/1990    Cook et al.
(Continued)

FOREIGN PATENT DOCUMENTS

WO    2005018687 A2    3/2005

OTHER PUBLICATIONS

Thomai Panagiotou et al.; Producing Micron- and Nano-Size Formulations for Functional Foods Applications; Functional Foods in Health and Disease; 2013; 17 pages; vol. 3, No. 7.
(Continued)

*Primary Examiner* — Anshu Bhatia
(74) *Attorney, Agent, or Firm* — Taft Stettinius & Hollister LLP

(57) ABSTRACT

A method for continuously processing at least two liquid feed streams is provided. A system for continuously processing at least two liquid feed streams is also provided.

59 Claims, 9 Drawing Sheets

(51) Int. Cl.

| | |
|---|---|
| *A61K 9/107* | (2006.01) |
| *A61K 31/05* | (2006.01) |
| *A61K 31/4545* | (2006.01) |
| *A61K 31/496* | (2006.01) |
| *A61K 31/55* | (2006.01) |
| *A61K 31/7048* | (2006.01) |
| *A61K 47/10* | (2017.01) |
| *A61K 47/12* | (2006.01) |
| *A61K 47/14* | (2017.01) |
| *A61K 47/24* | (2006.01) |
| *A61K 47/44* | (2017.01) |
| *B01F 3/08* | (2006.01) |
| *B01F 5/06* | (2006.01) |
| *B01F 13/00* | (2006.01) |
| *B01F 15/02* | (2006.01) |
| *B01F 15/06* | (2006.01) |
| *B01J 19/00* | (2006.01) |

(52) U.S. Cl.
CPC ............ *A61K 31/496* (2013.01); *A61K 31/55* (2013.01); *A61K 31/7048* (2013.01); *A61K 47/10* (2013.01); *A61K 47/12* (2013.01); *A61K 47/14* (2013.01); *A61K 47/24* (2013.01); *A61K 47/44* (2013.01); *B01F 3/0811* (2013.01); *B01F 5/061* (2013.01); *B01F 13/0059* (2013.01); *B01F 15/00344* (2013.01); *B01F 15/0243* (2013.01); *B01F 15/065* (2013.01); *B01J 19/0093* (2013.01); *B01F 2003/0842* (2013.01); *B01F 2015/062* (2013.01); *B01F 2215/0036* (2013.01); *B01J 2219/0086* (2013.01); *B01J 2219/00792* (2013.01); *B01J 2219/00873* (2013.01); *B01J 2219/00889* (2013.01); *B01J 2219/00891* (2013.01)

(56) References Cited

U.S. PATENT DOCUMENTS

| | | | |
|---|---|---|---|
| 5,314,506 | A | 5/1994 | Midler, Jr. et al. |
| 5,578,279 | A | 11/1996 | Dauer et al. |
| 6,159,442 | A | 12/2000 | Thumm et al. |
| 6,186,193 | B1 | 2/2001 | Phallen et al. |
| 6,558,435 | B2 | 5/2003 | Am Ende et al. |
| 6,977,085 | B2 | 12/2005 | Werling et al. |
| 7,829,039 | B2 | 11/2010 | Schubert et al. |
| 8,187,554 | B2 | 5/2012 | Panagiotou et al. |
| 8,367,004 | B2 | 11/2013 | Panagiotou et al. |
| 2003/0206959 | A9 | 11/2003 | Kipp et al. |
| 2004/0266890 | A1 | 12/2004 | Kipp et al. |
| 2006/0151899 | A1 | 7/2006 | Kato et al. |
| 2009/0269250 | A1* | 10/2009 | Panagiotou .......... B01J 19/0093 422/129 |

OTHER PUBLICATIONS

Thomai Panagiotou et al.; Improving Product Quality with Entrapped Stable Emulsions: From Theory to Industrial Application; Challenges; 2012; 30 pages; vol. 3.
T. Panagiotou et al.; Microfluidics Reaction Technology (MRT) for Continuous Production for Nano-Formulations of Drug Entities and Advanced Materials; Nanoformulation; 2012; 15 pages.
Thomai Panagiotou et al.; Form Nanoparticles via Controlled Crystallization; Reactions and Separations; CEP; Oct. 2008; 9 pages.
T. Panagiotou et al.; Production of Stable Drug Nanosuspensions Using Microfluidics Reaction Technology NSTI—Nanotech; 2007; 4 pages. vol. 4.
Thomai Panagiotou; Stable Micron- or Nano-Sized Suspensions; Ingredients & Formulation; Innovations in Pharmaceutical Technology; 2009; 3 pages; Issue 44.
Thomai Panagiotou et al.; Production of Norfloxacin Nanosuspensions Using Microfluidics Reaction Technology through Solvent/Antisolvent Crystalllization; I&EC Research; Ind. Eng. Chem. Res.; 2009; 12 pages; vol. 48.
Thomai Panagiotou et al.; Enhanced Transport Capabilities via Nanotechnologies: Impacting Bioefficacy, Controlled Release Strategies, and Novel Chaperones; Journal of Drug Delivery; 2011; 14 pages; vol. 2011.
T. Panagiotou et al.; Production of Nanoemulsions at Relevant Industrial Rates: Innovative Scale-up Strategies; TechConnect Briefs; 2019; 4 pages.
Thomai Panagiotou et al.; Bottom up Nano-Particle Formulation via Controlled Crystallization and Chemical Reactions; MRS Proceedings; 2011; 12 pages.
T. Panagiotou et al.; Production of Polymer Nanosuspensions Using Microfluidizer Processor based Technologies; NSTI—Nanotech; 2008; 4 pages; vol. 1.
Fuguo Liu et al.; Fabrication of Concentrated Fish Oil Emulsions Using Dual-Channel Microfluidization; Impact of Droplet Concentration on Physical Properties and Lipid Oxidation; Journal of Agricultural and Food Chemistry; 2016; 10 pages; vol. 64.
Long Bai et al.; Fabrication of Oil-in-Water Nanoemulsions by Dual-Channel Microfluidization Using Natural Emulsifiers: Saponins, Phospholipids, Proteins, and Polysaccharides; Elsevier; Food Hydrocolloids; 2016; 10 pages; vol. 61.
Thomai Panagiotou et al.; Optimizing Nanoemulsions Using High Shear Fluid Processing: Experimental and Modeling Methods; Microfluidics; www.microfluidicscorp.com; 1 page.
Christopher Earls Brennen; Cavitation and Bubble Dynamics; Oxford University Press; 1995; 254 pages.
Canadian Office Action; Canadian Intellectual Property Office; Canadian Patent Application No. 3,075,827; dated May 21, 2020; 4 pages.
International Search Report; ISA/US; International Application No. PCT/US2019/038705; dated Sep. 12, 2019; 2 pages.
Written Opinion of the International Searching Authority; ISA/US; International Application No. PCT/US2019/038705; dated Sep. 12, 2019; 3 pages.
International Preliminary Report on Patentability; ISA/US; International Application No. PCT/US2019/038705; dated Dec. 22, 2020; 4 pages.
Israeli Office Action; Israel Patent and Trademark Office; Israeli Application No. 273251; dated Mar. 2, 2021; 2 pages.

* cited by examiner

APPARATUS, SYSTEMS, AND METHODS FOR CONTINUOUS MANUFACTURING OF NANOMATERIALS AND HIGH PURITY CHEMICALS

CROSS-REFERENCE TO RELATED APPLICATIONS

This patent application is a U.S. National Phase of International PCT Application No. PCT/US2019/038705 filed on Jun. 24, 2019, which claims priority to U.S. Provisional Pat. Appln. Ser. No. 62/688,755 filed on Jun. 22, 2018 and U.S. Provisional Pat. Appln. Ser. No. 62/788,298 filed on Jan. 4, 2019, the contents of each application are incorporated herein by reference in their entireties.

FIELD OF THE DISCLOSURE

The present disclosure is directed to apparatus, systems, and methods that facilitate highly effective molecular contact within a defined reaction chamber, thereby enhancing and/or promoting a host of mixing and/or reaction phenomena. More particularly, the disclosed apparatus, systems, and methods are designed to enhance mixing of continuous streams of liquids that are fed into a microreactor so as to produce nanomaterials, enhance the rates of chemical reactions, or improve the purity of the products of the chemical reactions.

BACKGROUND

The role of hydrodynamics should not be underestimated in any facet of the engineering sciences. The flow patterns within process units and their associated transfer lines have a significant impact upon mass, energy and momentum transport rates and reaction proficiency. Thus, system designs generally benefit from the identification of energy dissipation mechanisms and, thus, quantification of the intensity of mixing and contact efficacy. These factors are generally important in materials handling and manufacturing processes.

For example, the intensity of turbulence generally influences the size of particles that are dispersed throughout a fluid, the quality of an emulsion, and the residence time distribution profiles that determine progress and selectivity of chemical reactions. This is particularly apparent in the emerging nanotechnologies, where precipitation and crystallization processes have a significant impact on product quality. Furthermore, mixing characteristics influence and/or determine the performance of reaction vessels, at both laboratory and production scales, and properly designed/implemented mixing systems can permit and/or facilitate the use of continuous systems, in lieu of batch systems, to enhance productivity.

In terms of mixing technologies, cavitation has been used in industry for homogenization operations, i.e., to disperse suspended particles in colloidal liquids. Numerous engineering principles are involved with cavitation behavior (see, e.g., Christopher Earls Brennen, "Cavitation and Bubble Dynamics", Oxford University Press (1995)). Although cavitation-based mixing is often employed with solids, it may not be the best choice for generation of nanoemulsions and vesicle loading, as in drug chaperones. Cavitation can result in issues associated with materials of construction and/or scale-up issues for mixing device fabrication. In particular, by forcing a liquid through an annular opening that has a narrow entrance orifice with a much larger exit orifice, a dramatic decrease in pressure results in fluid acceleration into a larger volume and generation of cavitation bubbles. The surface upon which these bubbles collide (causing their implosion) is subjected to tremendous stresses. Thus, materials such as polycrystalline diamond and stainless steel are generally required. High pressure homogenizers utilize high shear to create small particles. The technologies described hereinabove require multi-step processes and are energy intensive. Such technologies require first mixing all of the ingredients with a relatively low energy device and then processing with a high pressure homogenizer of a cavitation device several times, until the product quality is achieved.

Beyond mixing-related issues, a large number of compounds with potentially high pharmacological value fail to pass initial screening tests because such compounds are too hydrophobic to be effectively formulated. Most formulation strategies aim at increasing the bioavailability of such drugs by particle size reduction, as described extensively in the literature. Such strategies include the production of emulsions, liposomes and functionalized chaperones by high shear processing, the production of nanosuspensions by milling, micronization or high shear processing, and the production of nanoporous materials.

Nano-emulsions, liposomes and other generalized cargo loaded systems can only encapsulate a limited amount of drug. Therefore, current approaches may not be the strategies of choice for drugs with high dosage demands. Nanosuspensions can deliver much larger amounts of drug in a smaller volume than solvent-diluted drug systems and, therefore, may have a potential advantage as a formulation strategy when a high dose is required. Further, these conventional methods have high energy demands and are multi-step.

Most often, nanosuspensions are produced by milling, micronizing or high shear processing. Thus, current methods for manufacturing nanosuspensions primarily rely on the reduction of particle size of drug powders in dry or wet formulations. Such "top-down" processes are generally slow, require repetitive processing cycles, and require substantial energy. Indeed, the targeted particle sizes, usually less than 0.5 microns, are often time consuming and expensive to produce, frequently requiring repetitive processing cycles/passes through the milling/high shear equipment to achieve desired particle size distributions.

Controlled crystallization of drugs is an alternative to the production of drug nanosuspensions through size reduction techniques for generating desired particle size distributions. Crystallization is a method that is used to produce fine chemicals and pharmaceuticals of desired purity and/or for the formation of a specific crystal polymorph with desired crystalline structure and associated properties. However, current crystallization techniques typically produce particles in the range of several microns which are not suitable for delivering highly hydrophobic drugs. More recently, methods for production of nanosuspensions through crystallization have been proposed, but they have not demonstrated the necessary productivity robustness. In particular, the newer procedures lack the control that is required at the various mechanistic steps of crystallization (nucleation rate through crystal morphology and stabilization), process scalability and general applicability.

The patent literature describes processing equipment for particle size control and manipulation. For example, commonly assigned U.S. Pat. Nos. 4,533,254 and 4,908,154 to Cook et al. describe processing systems and apparatus having particular utility in emulsion and microemulsion processing. Flow streams are forced under pressure to impinge in a low-pressure turbulent zone. The disclosed systems/apparatus include a plurality of nozzles that effect impingement of flow sheets along a common liquid jet interaction front.

Greenwood et al. disclose a sterilizable particle-size reduction apparatus in WO 2005/018687. Kipp et al. disclose methods/apparatus for generating submicron particle suspensions that involves mixing a solution that contains a pharmaceutically active compound that is dissolved in a water-miscible solvent with a second solvent to form a pre-suspension of particles and then energizing the mixture to form a particle suspension having an average particle size of less than 100 μm (see U.S. Patent Publications 2003/0206959 and 2004/0266890; U.S. Pat. No. 6,977,085).

In the field of crystallization, the patent literature includes various teachings from the pharmaceutical industry. For example, U.S. Pat. No. 5,314,506 to Midler, Jr. et al. discloses the use of impinging jets to achieve high intensity micromixing of fluids so as to form a homogeneous composition prior to the start of nucleation in a continuous crystallization process. Nucleation and precipitation are initiated by utilizing the effect of temperature reduction on the solubility of the compound to be crystallized in a particular solvent (thermoregulation), or by taking advantage of the solubility characteristics of the compound in solvent mixtures, or a combination thereof. U.S. Pat. No. 5,578,279 to Dauer et al. discloses a dual jet crystallizer apparatus that includes a crystallization or mixing chamber having opposed angularly disposed jet nozzles. The nozzles deliver the compound to be crystallized and a crystallization agent. U.S. Pat. No. 6,558,435 to Am Ende et al. discloses a process for synthesis/crystallization of a pharmaceutical compound that involves contacting diametrically opposed liquid jet streams, such that the liquid streams meet at a point of impingement to create a vertical impingement film and create turbulence at their point of impact under conditions of temperature and pressure which permit reaction of reactive intermediates to produce a product. The jet streams are disclosed to have sufficient linear velocity to achieve micromixing of the jet stream constituents, followed by reaction and nucleation to form high surface area crystals. See also U.S. Patent Publication No. 2006/0151899 to Kato et al.

More recently, U.S. Pat. Nos. 8,187,554 and 8,367,004 to Panagiotou et al. describe apparatus, systems, and methods for achieving interaction of constituents within an interaction chamber to promote mixing and/or reaction phenomena. Unfortunately, however, the apparatus, systems, and methods disclosed in the '554 and '004 patents have significant shortcomings. One shortcoming is such apparatus, systems, and methods result in a nano- or micro-particle formulation having incorrect proportions of constituents. The apparatus, systems, and methods of the '554 and '004 patents describe two feed streams that are directly fed to an intensifier pump at different individually actively controlled rates such that interaction between the two feed streams is substantially prevented prior to pressurization within the intensifier pump, thereby, avoiding potential reactions and other constituent interactions prior to micro- and/or nano-scale interactions within the interaction chamber described therein. Thus, such a system uses a first pump to control a first feed stream, a second pump to control a second feed stream, and an intensifier pump to control the mixture of first feed stream and the second feed stream (i.e., the inputs and outputs are being controlled). In theory, it would seem advantageous to actively control the flow rate of the system by actively controlling each feed stream (e.g., attempting to have each feed stream enter the system, flow through the system, and exit the system at the same flow rate). However, in practice, it is very difficult and, in most applications, not possible to control enough equipment and processes in the system to achieve such a sufficient flow rate. Such difficulties arise because the flow rates are pulsating rather than being completely constant, which results in a sufficient flow rate not being achieved. In such a system, the flow rate is a processing rate that is too low or too high. Such an insufficient flow rate results in a disruption of the desired ratio of the constituents of the feed streams and ultimately failure to achieve the desired micro- and/or nano particle formulation. Additionally, a lack of control of the flow rate of the system can make scale up very problematic.

Another shortcoming is that a primary goal of the apparatus, systems, and methods disclosed in the '554 and '004 patents is to keep the first and second feed streams separate until entering an intensifier pump (i.e., to prevent pre-mixing of the first and second feed streams). The first and second feed streams mix when such streams enter the intensifier pump. However, it is difficult, and in many cases not possible, to control the mixing in the intensifier pump. Such a lack of control results in the creation of blobs of constituents, especially if the constituents consist of immiscible liquids. This is a significant problem because reaction chambers have very small internal volume. In an example involving water and oil, blobs of only water or only oil may flow from an intensifier pump to a reaction chamber. However, a homogenous mixture of oil and water in a particular ratio would generally be desired. If the system passes blobs of oil and/or water through the reaction chamber, the resulting micro- or nano-particles will be too large and will not have the desired ratio. The low processing rates of the system will also lead to the blobs plugging the microchannels in the reaction chamber, which would make such a system unsuitable for large scale production, especially in the chemical and pharmaceutical industries.

A further shortcoming is that the apparatus, systems, and methods disclosed in the '554 and '004 patents provide insufficient time to achieve certain desired processes and chemical reactions. For example, the first and second feed streams only pass through an intensifier pump and a reaction chamber. A typical residence time for an intensifier pump is commonly about 1 or 2 seconds but a process may require as high as about 40 seconds. A common residence time for a reaction chamber is about 1 millisecond. Given such a minimal time frame to conduct a process in the apparatus, systems, and methods disclosed in the '554 and '004 patents, many desirable processes and chemical reactions that require more time would not be possible.

Despite efforts to date, a need remains for systems/apparatus and methods that are effective in producing nanoparticles. Systems/apparatus and processes for generation of nanoparticles in an efficient, continuous and reliable manner are also needed. Beyond nanoparticle processing, there remains a need for systems/apparatus and methods that are effective in facilitating various materials processing operations, e.g., reaction, emulsion and/or crystallization processes, by, inter alia, minimizing diffusion limitations to requisite interaction between reactants and/or crystallizing constituents. Still further, a need remains for systems and methods that yield desirable particle size distributions, morphology and/or compositions/phase purities through effective process design and/or control. Indeed, a need remains for systems and methods that effectively control interfacial reaction/contact between constituents to achieve desired processing results, e.g., to reduce the potential for undesirable side reactions.

SUMMARY

The present disclosure addresses the problems described above by providing the disclosed systems/apparatus and methods for continuously processing at least two liquid feed streams. One aspect of the present disclosure provides a method for continuously processing at least two liquid feed streams. In some embodiments, the method comprises: pumping a first feed stream to an in-line mixer at an actively automatically controlled rate; flowing a second feed stream to the in-line mixer; mixing the first and second feed streams to achieve a substantially homogeneous mixture; pumping the substantially homogeneous mixture to a high pressure pump at an actively controlled rate; pressurizing the substantially homogeneous mixture within the high pressure pump to an elevated pressure of at least 35 MPa; and delivering the substantially homogeneous mixture to a microreactor downstream from the high pressure pump. In some embodiments, the microreactor has a minimum channel dimension of 500 microns or less, causing the first and second liquid streams to interact within the microreactor at a nanoscale level.

In some embodiments, the first feed stream includes a first constituent and the second feed stream includes a second constituent. In some embodiments, the first and second feed streams are delivered to the in-line mixer in feed lines that are coaxially aligned. In some embodiments, the first and second feed streams are introduced to the in-line mixer through spaced ports defined by the in-line mixer. In some embodiments, the actively controlled rate for delivery of the first feed stream to the in-line mixer is effected by an actively controlled feed pump for the first feed stream. In some embodiments, the method further comprises cooling or quenching the substantially homogenous mixture after interaction within the microreactor.

In some embodiments, the first constituent includes a solvent and the second constituent includes an antisolvent. In some embodiments, interaction of the solvent and the antisolvent in the microreactor is effective to define a nanosuspension. In some embodiments, the method further comprises obtaining constituent nanoparticle crystals from the nanosuspension. In some embodiments, the solvent stream is selected from the group consisting of dimethyl sulfoxide (DMSO), N-Methyl-2-Purrolidone (NMP), methanol, ethanol, acetone, dichloromethane, octanol and isopropyl alcohol. In some embodiments, the antisolvent stream is selected from the group consisting of water, hexane and heptane. In some embodiments, the solvent stream is DMSO and nanoparticles of azithromycin are obtained at a median particle size of about 50-100 nm. In some embodiments, the solvent stream is DMSO and nanoparticles of oxycarbazepine are obtained at a median particle size less than 1000 nm. In some embodiments, the solvent stream is DMSO or NMP and nanoparticles of loratadine are obtained at a median particle size of less than 500 nm. In some embodiments, the method further comprises cooling or quenching the nanosuspension after interaction within the microreactor.

In some embodiments, the elevated pressure is at least about 70 MPa. In some embodiments, the elevated pressure is at least about 140 MPa. In some embodiments, the elevated pressure is at least about 207 MPa. In some embodiments, the ratio of the flow rate of the second stream to the flow rate of the first stream is at least about 2:1. In some embodiments, the ratio of the flow rate of the second stream to the flow rate of the first stream is at least about 3:1. In some embodiments, the ratio of the flow rate of the second stream to the flow rate of the first stream is at least about 10:1.

In some embodiments, the microreactor has channels with minimum dimensions in the range of 10-500 microns. In some embodiments, the average fluid velocity in microreactor channels is in the range of 300-500 m/s. In some embodiments, the method further comprises effecting a sheer rate in the microreactor of at least about $1.2 \times 10^6$ $s^{-1}$. In some embodiments, the microreactor has a single slot geometry.

In some embodiments, at least one of the liquid feed streams includes solid particles. In some embodiments, at least one of the feed streams contains seed particles. In some embodiments, at least one of the feed streams contains catalyst particles. In some embodiments, the first constituent is a first reactant and the second constituent is a second reactant. In some embodiments, the method further comprises adjusting reaction selectivity by controlling interaction between the first and second reactants prior to the nanoscale level interaction within the microreactor. In some embodiments, control of the interaction between the first and second reactants is effected by encouraging contact between the first and second reactants in the in-line mixer prior to pressurization in the high pressure pump so as to achieve the substantially homogeneous mixture. In some embodiments, the substantially homogeneous mixture is pumped to the high pressure pump through a port defined by the high pressure pump. In some embodiments, the method further comprises cooling or quenching the substantially homogeneous mixture after reaction within the microreactor.

In some embodiments, the first and second feed streams are immiscible. In some embodiments, the first and second feed streams are miscible. In some embodiments, the constituents interact within the microreactor to achieve an emulsion, a dispersion, a liposomal formulation, lipid nanoparticles, or a crystalline or amorphous material. In some embodiments, the first feed stream is an oil phase and the second feed stream is a water phase. In some embodiments, the oil phase is selected from a vegetable oil, a nut oil, an animal oil, an inorganic oil, a lipid, a surfactant, a polymer, an active ingredient, a flavoring, a coloring, an alcohol, an organic solvent, and/or a derivative thereof. In some embodiments, the water phase is selected from water, lipid, surfactant, viscosity modifier, pH adjuster, and sugar. In some embodiments, the first feed stream is a water phase and the second feed stream is an oil phase. In some embodiments, the oil phase is selected from a vegetable oil, a nut oil, an animal oil, an inorganic oil, a lipid, a surfactant, a polymer, an active ingredient, a flavoring, a coloring, an alcohol, an organic solvent, and/or a derivative thereof. In some embodiments, the water phase is selected from water, lipid, surfactant, viscosity modifier, pH adjuster, and sugar.

Another aspect of the present disclosure provides a system for continuously processing at least two liquid feed streams. In some embodiments, the system comprises a feed pump that is adapted to pump a first feed stream downstream at an actively automatically controlled rate; an in-line mixer positioned to receive the first feed stream from the feed pump and a second feed stream from a feed line; a high pressure pump positioned to receive the substantially homogeneous mixture from the in-line mixture; and a microreactor downstream of the high pressure pump. In some embodiments, the in-line mixer is adapted to mix the first and second feed streams to achieve a substantially homogeneous mixture. In some embodiments, the microreactor has a minimum channel dimension of 500 microns or less. In some embodiments, the microreactor is adapted to effect high shear fields so as to achieve thorough mixing of the substantially homogeneous mixture.

In some embodiments, the feed pump is a metering pump. In some embodiments, the first and second feed streams are delivered to the in-line mixer in a coaxial arrangement. In some embodiments, the microreactor has a single slot geometry. In some embodiments, the system further comprises a cooling unit downstream of the microreactor. In some embodiments, the in-line mixer includes a plurality of spaced feed ports. In some embodiments, the first feed stream is introduced to the in-line mixer through a first feed port and the second feed stream is introduced to the in-line mixer through a second feed port.

In some embodiments, the first feed stream includes a first constituent and the second feed stream includes a second constituent. In some embodiments, the microreactor is adapted to effect a controlled nanoscale interaction between the first constituent and the second constituent. In some embodiments, the microreactor is adapted to effect interaction of a first reactant in the first feed stream and a second reactant in the second feed stream at a nanoscale level. In some embodiments, the system is configured so that reaction selectivity can be controlled by controlling interaction between the first and second reactants prior to the nanoscale level interaction within the microreactor. In some embodiments, control of the interaction between the first and second reactants is effected by encouraging contact between the first and second reactants in the in-line mixer prior to pressurization in the high pressure pump so as to achieve the substantially homogeneous mixture. In some embodiments, the first and second reactants are delivered to the in-line mixer through spaced ports defined by the in-line mixer.

In some embodiments, the elevated pressure is at least about 70 Mpa. In some embodiments, the elevated pressure is at least about 140 MPa. In some embodiments, the elevated pressure is at least about 207 MPa.

In some embodiments, the ratio of the flow rate of the second stream to the flow rate of the first stream is at least about 2:1. In some embodiments, the ratio of the flow rate of the second stream to the flow rate of the first stream is at least about 3:1. In some embodiments, the ratio of the flow rate of the second stream to the flow rate of the first stream is at least about 10:1.

In some embodiments, the microreactor has channels with minimum dimensions in the range of 10-500 microns. In some embodiments, the average fluid velocity in microreactor channels is in the range of 300-500 m/s. In some embodiments, the sheer rate effected in the microreactor is at least about $1.2 \times 10^6$ $s^{-1}$. In some embodiments, the microreactor has a single geometry.

Micro-scale apparatus, systems and methods are provided according to the present disclosure that facilitate and utilize microreactor technology to achieve desired mixing and interaction at a micro and/or molecular level between and among feed stream constituents. The disclosed apparatus, systems and methods are capable of various degrees of mixing intensity and control of energy dissipation mechanisms, thereby maximizing useful work in forming surfaces and interfaces between and among constituent molecules/compounds. The present disclosure permits advantageous reductions in system entropy that might be otherwise experienced due to process inefficiencies. Such entropy reduction is a major benefit standing alone, but also translates to minimizing energy lost to heat, sound, light and cavitation. Indeed, reduced system entropy advantageously further translates to a reduced propensity for component damage.

Furthermore, the disclosed apparatus, system and methods advantageously facilitate and/or support process intensification, thereby miniaturizing unit operations and processes through both scale reduction and integration of operational steps, e.g., mixing, reaction and separation unit operations. Consequently, processes utilizing the disclosed apparatus, systems and methods offer enhanced efficiency and cost effectiveness. In addition, exemplary embodiments/implementations of the disclosed apparatus, systems and methods are adapted to function in environments that require portability, thereby providing enhanced flexibility in applications and in-use time.

The disclosed apparatus, systems and methods make it possible to overcome the limitations of prior art systems through precise control of energy input and dissipation mechanisms that dictate/control process pathways and rates. For example, in an exemplary implementation of the present disclosure, solvent composition may be used to affect supersaturation conditions, e.g., through addition of a miscible non solvent. In further exemplary implementations of the present disclosure, a process/method is provided that employs a solvent/anti-solvent crystallization technique in conjunction with the disclosed apparatus/system to produce advantageous drug nanosuspensions. As compared to micromixing models reported in the literature, turbulent energy dissipation rates attainable in the disclosed reaction chambers/microreactors are on the order of $10^7$ W/kg and higher. The disclosed apparatus/system thus achieves rapid micromixing (time scale 4 μs) and meso-mixing (time scale 20 μs), with a nominal residence time in the reaction chamber that is on the order of 1 ms. In addition, mixing at the nanometer scale provides a uniform supersaturation ratio which is a major controlling factor in crystal formation and growth. Controlling the timing and location of the mixing of the solvent and anti-solvent streams provides control of the onset of the nucleation process. This control, in combination with a homogeneous supersaturation ratio, results in desirably uniform crystal growth and stabilization rates.

Numerous processes may benefit through use/implementation of the disclosed apparatus and systems. In particular, process implementations benefit, at least in part, based on an ability to maximize the degree to which input energy is desirably directed to forming/establishing interaction surfaces and interfaces. Turbulence and surface tension forces achieved according to the present disclosure are advantageously effective in initiating nano-scale events, such as formation of stable nano-emulsions and formation of sufficient molecular clustering to create/establish homogeneous nucleation sites for crystal growth. Exemplary applications/implementations of the present disclosure also include, but are not limited to, selectivity enhancement in competitive reaction networks, control of size of dispersed solids (whether from reactive precipitation, crystallization and/or declustering), control of crystalline drug polymorph selectivity, and formation of chaperone systems via encapsulation of active ingredients.

The foregoing phenomena are important parameters for reactions/systems that are limited and/or controlled by mass transfer rates/performance. Thus, the present disclosure advantageously facilitates formation of critical sized clusters that become homogeneous nucleation sites for crystal growth via high degrees of local super-saturation. Such nucleation sites influence the molecular diffusion processes forming surfaces, their growth rates, integration of various molecular species into the surface, and ultimate size and purity of the particles formed.

The foregoing molecular species may form various polymorphs, and the desired form can be obtained through manipulation of operational parameters, e.g., microreactor design, microreactor geometry, pressure generated by the high pressure pump, supersaturation ratio, solvents, antisolvents, temperature and combinations thereof. Mass transfer limitations in multiphase reacting systems can be overcome according to the present disclosure, e.g., in the production of biodiesel, because the liquid reactants have limited solubility in each other and, therefore, an interfacial reaction must occur during an initial "lag phase." The rate of such interfacial reaction may be enhanced by dispersing small droplets of one phase into the other, greatly improving the interfacial surface area to volume ratio.

The same phenomenon is noted when heterogeneous reactions involving solid particles are involved. In particular, a surface-to-volume enhancement accelerates turnover rates proportional to surface area availability, whether the surface is catalytic or a reactant. Moreover, boundary layer resistances are reduced as particle size is reduced, once again promoting reaction rates up to their fundamental/intrinsic rates. This phenomenon is also applicable when interfacial mass transfer limits downstream separation processes, e.g., for downstream extraction, absorption, and adsorption processes, and for formation of stable emulsions, with or without surface active agents, since droplets at nano scale sizes, although thermodynamically unstable, can exist for lengthy time scales due to an extremely slow kinetics response.

Chaperone systems, such as with immiscible fluids or isolation requirements from the continuous phase (as in targeting for imaging and/or drug delivery) are readily prepared via the present disclosure using surface active agents as the encapsulate and, due to minimization of potential heat effects while processing vesicles, heat liable surface active agents, such as those with protein functionality, can be utilized. The high shear forces associated with the disclosed reaction chambers can be beneficial when shear thinning or thickening behavior is to be exploited during processing.

In addition, the present disclosure facilitates encapsulation down to the nano-scale of hydrophobic substances within amphi-morphic surfactants for dispersion in hydrophilic environments (or vice versa), as in nutraceutics, pharmaceutics, and cosmetics, among others. The encapsulates can also be useful in functionalizing membranes and providing "smart" characteristics; for example, as (a) sequestering agents in guard systems, (b) controlled release of growth factors in tissue engineering applications, (c) soluble gas transport enhancement, and (d) in general sensor/recorder systems. The disclosed apparatus/systems and methods may be used to facilitate both fast and slow processes, and to facilitate chemical reactions and physical processes, such as crystallization.

Further, the present disclosures advantageously facilitates production of polymer nanosuspensions in the range of 50-500 nm using both emulsion and precipitation methods. By controlling processing parameters, nanosuspensions with various polymer sizes and densities may be created. The disclosed systems/methods may be used to provide active pharmaceutical ingredients (APIs) that are encapsulated or otherwise contained within a polymeric matrix. In this sense, the polymeric matrix functions as a "chaperone" for such API's. The polymeric matrix is generally amorphous and may advantageously define a biocompatible and/or bioabsorbable product. The feedstream for such processing techniques may include monomeric constituents, polymeric constituents or combinations thereof.

Exemplary processing roadmaps for processing regimens may be developed using the disclosed apparatus/systems. For example, roadmaps for drug crystallization may be developed as follows: (i) determine solvent, antisolvent and surfactant constituents based on applicable input criteria, e.g., solubilities, toxicities, compatibility and screening experiments; (ii) introduce the selected solvent, antisolvent and surfactant constituents to the disclosed apparatus/system to produce advantageous nanosuspensions based on applicable process variables, e.g., microreactor chamber design, pressure and supersaturation ratio; and (iii) purify the nanosuspension (if required) to recover crystallized drug, e.g., using centrifuge, filter, rinsing and/or lypholization techniques. The disclosed roadmaps may be used to yield crystallized particles characterized by desired particle sizes and particle size distributions.

More generally, roadmaps may be developed and implemented for various processing regimens according to the present disclosure. Exemplary methods may involve, inter alia:

a. Identifying a solvent or first reactant/continuous phase, and an antisolvent or second reactant/dispersed phase which together define a process stream;

b. Determining need for surfactant(s) to achieve desired stability/control of process stream;

c. Determining concentration of target molecule/species or reactants within solvent or process stream/dispersed phase, and ratio of solvent/antisolvent or reactants/continuous phase/dispersed phase to achieve a predetermined level of supersaturation or contact efficiency/efficacy to drive relevant mechanism, e.g., crystallization mechanism, reaction mechanism, emulsion mechanism, coating mechanism, etc.;

d. Introducing predetermined amount(s) of energy to the process stream;

e. Regulating energy dissipation mechanism(s) at specified locations within system;

f. Contacting the solvent/antisolvent, reactants or continuous/dispersed phases in a confined volume at a nanoscale so as to deliver product of a desired characteristic, e.g., products having a desired particle size distribution, morphology, composition and/or combinations thereof.

The present disclosure provides other advantages compared to other approaches in the art that have been utilized. One advantage of the apparatus, systems and methods according to some embodiments is that such apparatus, systems and methods yield high accuracy of the desired flow rates of each stream and the flow rate ratio of the two streams combined with the ability to adjust the flow rates and the flow rate ratio of the two streams in real time, which results in a micro- or nano-particle having the desired formulation. An advantage according to another embodiment is the ability to vary the residence times and therefore the interaction time of the two streams at will, which makes the system suitable for processes that require long interaction (tens of seconds) and for processes that required shorter interactions (fewer than ten seconds). An advantage according to another embodiment is that homogenous material entering the microreactor results in processes taking place under uniform conditions. Therefore, the final product is uniform in terms of particle size, particle composition, and structure. All of the advantages described in the present disclosure improve the ability to scale up the process, while maintaining the desired flow rates, flow rate ratios, and uniform conditions in the production of the final product.

Additional advantage features, functions and implementations of the disclosed apparatus, systems and methods will be apparent from the description which follows, particularly when read in conjunction with the appended figures.

BRIEF DESCRIPTION OF THE FIGURES

The above-mentioned aspects of embodiments will become more apparent and will be better understood by reference to the following description of the embodiments taken in conjunction with the accompanying drawings, wherein.

DETAILED DESCRIPTION

The present disclosure provides advantageous systems and methods for achieving effective contact/interaction of constituents within a defined chamber, i.e., a microreactor, to enhance and/or promote a host of mixing and/or reaction phenomena. Set forth herein below are descriptions of exemplary system designs and implementations, including exemplary implementations and beneficial results achieved thereby. Although the systems and methods of the present disclosure are described with reference to exemplary embodiments and implementations, it is to be understood that the present disclosure is not limited to such illustrative examples. Rather, the disclosed apparatus, systems and methods may take various physical forms and be applied to a multitude of processing schemes and environments, without departing from the spirit or scope of the present disclosure.

A. Exemplary Apparatus/System Design(s) and Exemplary Methods

Figure 1:
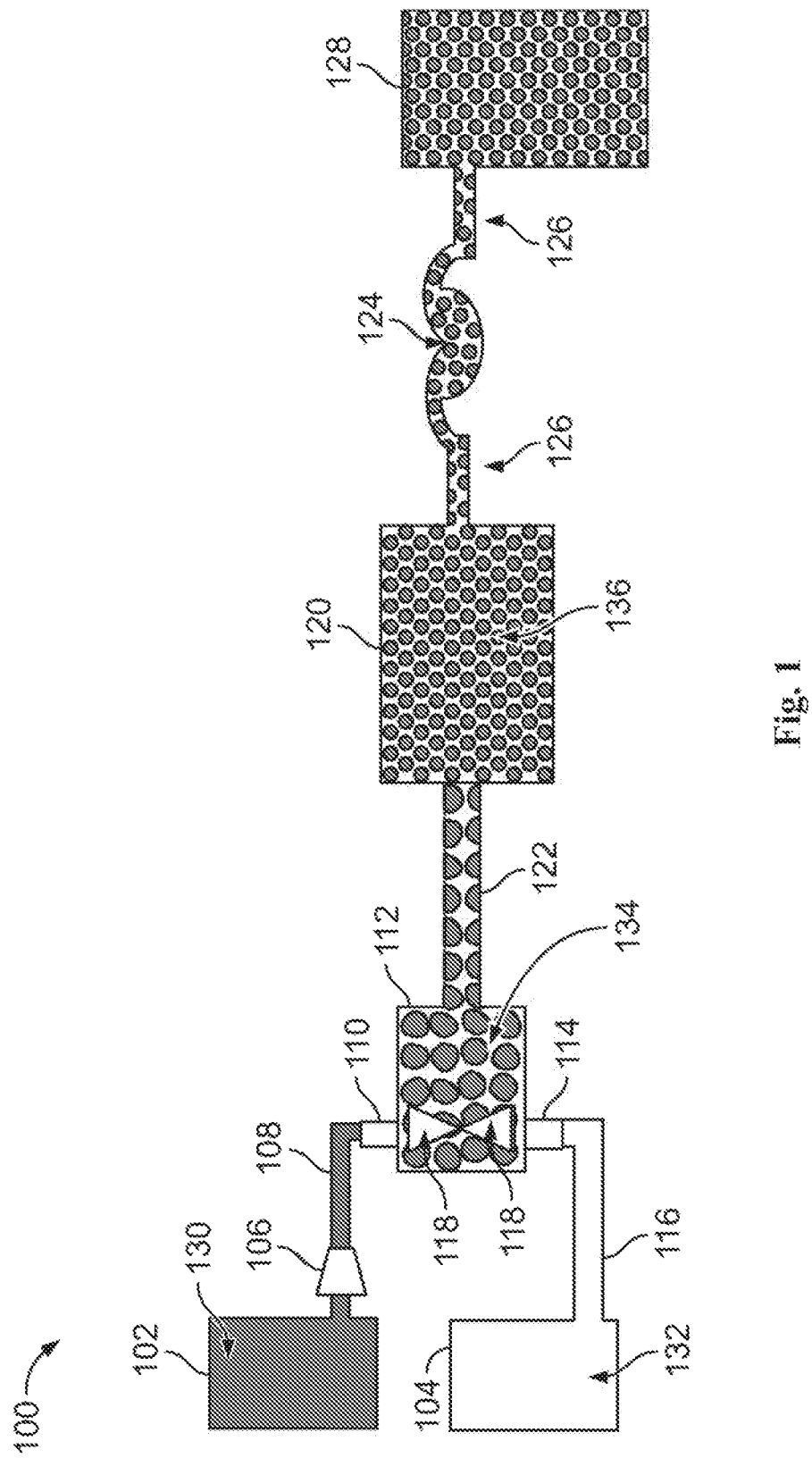
FIG. 1 shows a system for continuously processing at least two liquid feed streams in accordance with an embodiment of the present disclosure.

Referring now to FIG. 1, an illustrative system 100 for continuously processing at least two liquid feed streams in accordance with the present disclosure is schematically depicted. System 100 includes holding tank 102 and holding tank 104. In some embodiments, holding tank 102 and holding tank 104 are optional equipment. Holding tank 102 is adapted to hold a first liquid stream 130. Holding tank 104 is adapted to hold a second liquid stream 132. Holding tank 102 is connected to a pump 106 via a first feed line 108. In some embodiments, pump 106 is a metering pump, positive displacement pump, syringe pump, peristaltic pump, or piston pump. Pump 106 is connected to a first port 110 of an in-line mixer 112 via the first feed line 108. Holding tank 104 is connected to a second port 114 of an in-line mixer 112 via a second feed line 116.

In-line mixer 112 includes first port 110 and second port 114. In-line mixer 112 also includes mixing elements 118. In some embodiments, the in-line mixer is a T-mixer, a static mixer with baffles, a rotor-stator mixer, a propeller mixer, a co-axial orifice or an ultrasonic mixer, to name a few. Such in-line mixers have a variety of energy levels and mixing intensity. In-line mixer 112 is connected to a high pressure pump (not shown) via a conduit 122. High pressure pump (not shown) is connected to a microreactor 120 via a conduit 122. Microreactor 120 is connected to a heat exchange unit 124 via conduit 126. Heat exchange unit 124 is connected to a collection tank 128 via conduit 126. In some embodiments, the heat exchange unit 124 is optional equipment. In some embodiments, the microreactor 120 includes a heat exchange unit (not shown), and, in such embodiments, the heat exchange unit 120 would be unnecessary.

In the illustrative embodiment, pump 106 is capable of pumping first liquid stream 130 downstream to first port 110 of the in-line mixer 112 via first feed line 108. In some embodiments, the pumping moves a precise volume of first liquid stream 130 in a specified time period providing an accurate volumetric flow rate. In some embodiments, pump 106 is utilized to pump first liquid stream 130 downstream to in-line mixer 112 at an actively automatically controlled rate. In some embodiments, the actively automatically controlled rate is achieved based on operation of the individually controlled pump 106. Second liquid stream 132 flows downstream through the second port 114 via second feed line 116. In some embodiments, the flow rate of the second liquid stream 132 is controlled indirectly by the pumping action of the microreactor 120. The first liquid stream 130 and the second liquid stream 132 may take various forms and exhibit various properties according to the present disclosure. In some embodiments, the first liquid stream 130 and the second liquid stream 132 may be multiphase fluids, miscible fluids, or immiscible fluids. In some embodiments, the first liquid stream 130 and the second liquid stream 132 may contain particles and or may contain constituents that react with each other. In some embodiments, the manner in which the first liquid stream 130 and the second liquid stream 132 are processed and/or stored prior to introduction to system 100 may vary widely, with the disclosed reservoirs and feed lines being merely illustrative of pre-processing handling/storage of reactant/fluid streams. In some embodiments, a pump (not shown) is used to deliver the second liquid stream 132 downstream through the second port 114. First liquid stream 130 and second liquid stream 132 each have a pre-determined flow rate and composition. In some embodiments, the pump 106 is used to adjust the flow rate of the first liquid stream 130. In some embodiments, a valve or orifice (not shown) is used to adjust the flow rate of first liquid stream 130 and/or second liquid stream 132.

First liquid stream 130 and second liquid stream 132 mix in the in-line mixer 112 to form a substantially homogeneous mixture 134. As used herein, the term "substantially homogeneous mixture" means a mixture of two liquid streams that has the same or substantially similar proportion of its constituents throughout any given sample of the mixture. For example, when dividing the volume of a mixture of two liquid streams in half, the same or substantially similar amount of constituents are present in each half. In some embodiments, the composition of the constituents in the mixture of the two liquid streams may fluctuate slightly above or below the average composition of the constituents in the mixture.

The function of the in-line mixer is two-fold: (a) it forms a substantially homogeneous mixture 134 that can be introduced into the microreactor 120 and mixed further, and (b) various processes that start in the in-line mixer (i.e., crystallization, chemical reactions, etc.) have enough time to reach the desired state of completion at the exit of the microreactor 120. Generally, the in-line mixer 112 does not provide high enough energy to create nanoparticles 136; however, the microreactor 120 is employed to create nanoparticles 136. Therefore, the substantially homogenous mixture 134 is processed by the microreactor 120 since the microreactor 120 generates turbulent flow fields that have turbulent eddies as low as 20 nm. If the first liquid stream 130 and second liquid stream 132 contain species that react with each other, chemical reactions may take place inside these eddies resulting in nanometer size particles. If the first liquid stream 130 and second liquid stream 132 are immiscible, one of the liquid streams 130 or 132 may form nanosized droplets that are dispersed in the other liquid. If surfactants are used, the droplets may be stabilized forming nanoemulsions with a long shelf life.

In some embodiments, in-line mixer 112 is replaced with a tube (not shown) of sufficient length inside which the first liquid stream 130 and the second liquid stream 132 may mix to form a substantially homogenous mixture 134. In such embodiments, the mixing is the result of molecular diffusion and/or turbulence. In some embodiments, the time required for complete mixing may be calculated as a result of velocities in the tube, the type of flow in the tube (turbulent or laminar, single phase or multiphase), the dimensions of the tube, the diffusivity of the species and other physical properties, as well the pressure and temperature.

In the illustrative embodiment, the substantially homogeneous mixture 134 is pumped downstream from the in-line mixer 112 to the high pressure pump (not shown) via conduit 122. The high pressure pump is generally effective to pressurize the substantially homogenous mixture 134 to an elevated pressure, e.g., a pressure of up to 40,000 psi. As used herein, the term "high pressure pump" refers to a high pressure pump that is adapted to deliver high pressure output streams, e.g., 500 to 40,000 psi and higher. In some embodiments, the high pressure pump is an intensifier pump or a piston. An exemplary high pressure pump according to an embodiment includes a hydraulic pump and a piston that multiplies the system pressure therewithin. Thus, in such embodiment, the hydraulic pump may be effective to generate pressures of about 1500 to 3500 psi, and the piston mechanism may be effective to multiply such pressure by a factor of 0× to 30×. Each piston within a pressure assembly may be viewed as a distinct high pressure pump for purposes of the present disclosure. Exemplary high pressure pumps according to some embodiments of the present disclosure avoid cavitation, thereby minimizing potential energy dissipation associated therewith.

The substantially homogeneous mixture 134 is pumped downstream from the high pressure pump (not shown) to the microreactor 120 via conduit 122. The pumping action of the microreactor 120 pulls the second liquid stream 132 into the in-line mixer 112 (i.e., causes the flow of the second liquid stream 132 into the in-line mixer 112). In some embodiments, the microreactor 120 includes a pump (not shown) that maintains a certain pressure at a port (not shown) of the microreactor 120.

In some embodiments, the microreactor 120 is any commercial high pressure homogenizer, including, without limitation, with fixed geometry such as Microfluidics (Westwood, Mass., USA), DyHydromatics (Maynard, Mass., USA) and BEEI (South Easton, Mass., USA); valve homogenizers such as Niro Soavi (Parma, Italy), APV (PPXFLOW/ United Kingdom) and Avestin (Canada). High-pressure homogenizers are high energy level mixing devices and are, therefore, capable of producing nanoparticles. In the illustrative embodiment, microreactor 120 produces nanoparticles 136. The various homogenizers have different characteristics that make them suitable or unsuitable for different applications.

The nanoparticles 136 flow from the microreactor 120 to the heat exchange unit 124 via conduit 126. The heat exchange unit 124 is utilized to cool the nanoparticles 136. Nanoparticles 136 flow from heat exchange unit 124 to the collection tank 128 via conduit 126. Mixing highly affects the rates of phenomena that are responsible for forming the nanoparticles 136, including precipitation, crystallization, emulsification, or chemical reactions. These processes should be completed at the exit of the microreactor 120. If such processes are not completed at the exit of the microreactor 120, the nanoparticles 136 will continue to grow uncontrollably after the microreactor 120. To achieve completion of the intended process, the first liquid stream 130 and second liquid stream 132 should have sufficient contact time prior to being processed within the microreactor 120, which is facilitated by controlling the homogeneity of the mixture of the two liquid streams 130 and 132 via the in-line mixer 112 and the dimensions of the conduit 122 between the in-line mixer 112 and the microreactor 120.

In the illustrative embodiment, the pump 106 in combination with the high pressure pump (not shown) control the flow rate ratios of the two streams. The energy input to the fluid at different locations of the system is controlled by the geometry of the flow path. Thus, energy dissipation may be controlled/minimized through advantageous piping design/ layout, the design/geometry of the microreactor 120, and the design/layout of heat exchange unit 124 positioned downstream of the microreactor 120. Typically, energy dissipation is most strongly influenced by the design/geometry of the microreactor 120, e.g., through turbulence and/or shear associated therewith.

Figure 2:
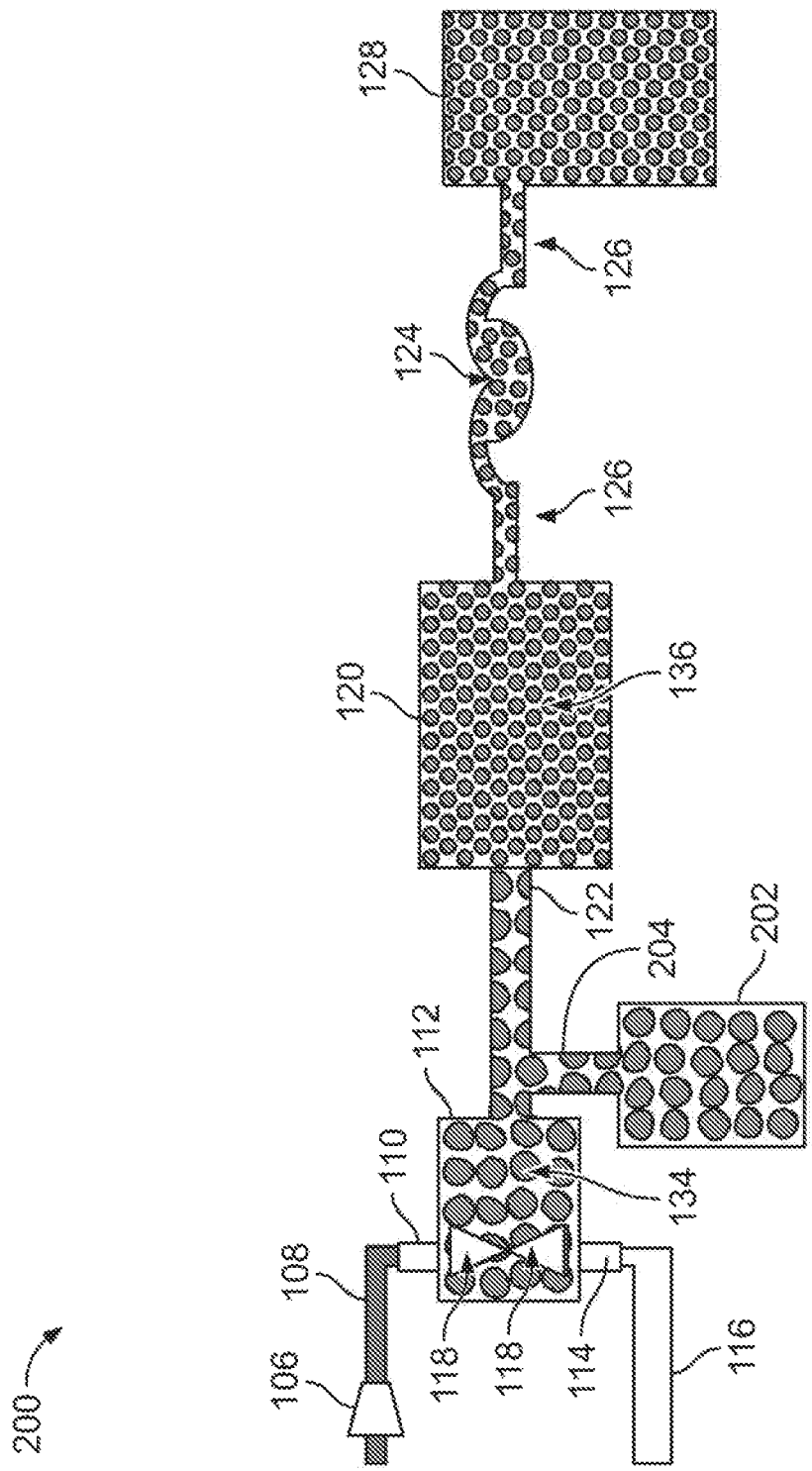
FIG. 2 shows a system for continuously processing at least two liquid feed streams in accordance with an embodiment of the present disclosure.

Referring now to FIG. 2, an illustrative system 200 for continuously processing at least two liquid feed streams in accordance with the present disclosure is schematically depicted. In-line mixer 112 is connected to conduit 122. Conduit 122 connects to conduit 204. Conduit 204 connects to overflow tank 202. In the illustrative embodiment, overflow tank 202 may optionally be located before and/or after the in-line mixer 112. In some embodiments, the overflow tank 202 is employed to ensure that both the in-line mixer 112 and the microreactor 120 operate at capacity. In some embodiments, some amount of substantially homogeneous mixture 134 flows into overflow tank 202 from conduit 122 via conduit 204.

Figure 3:
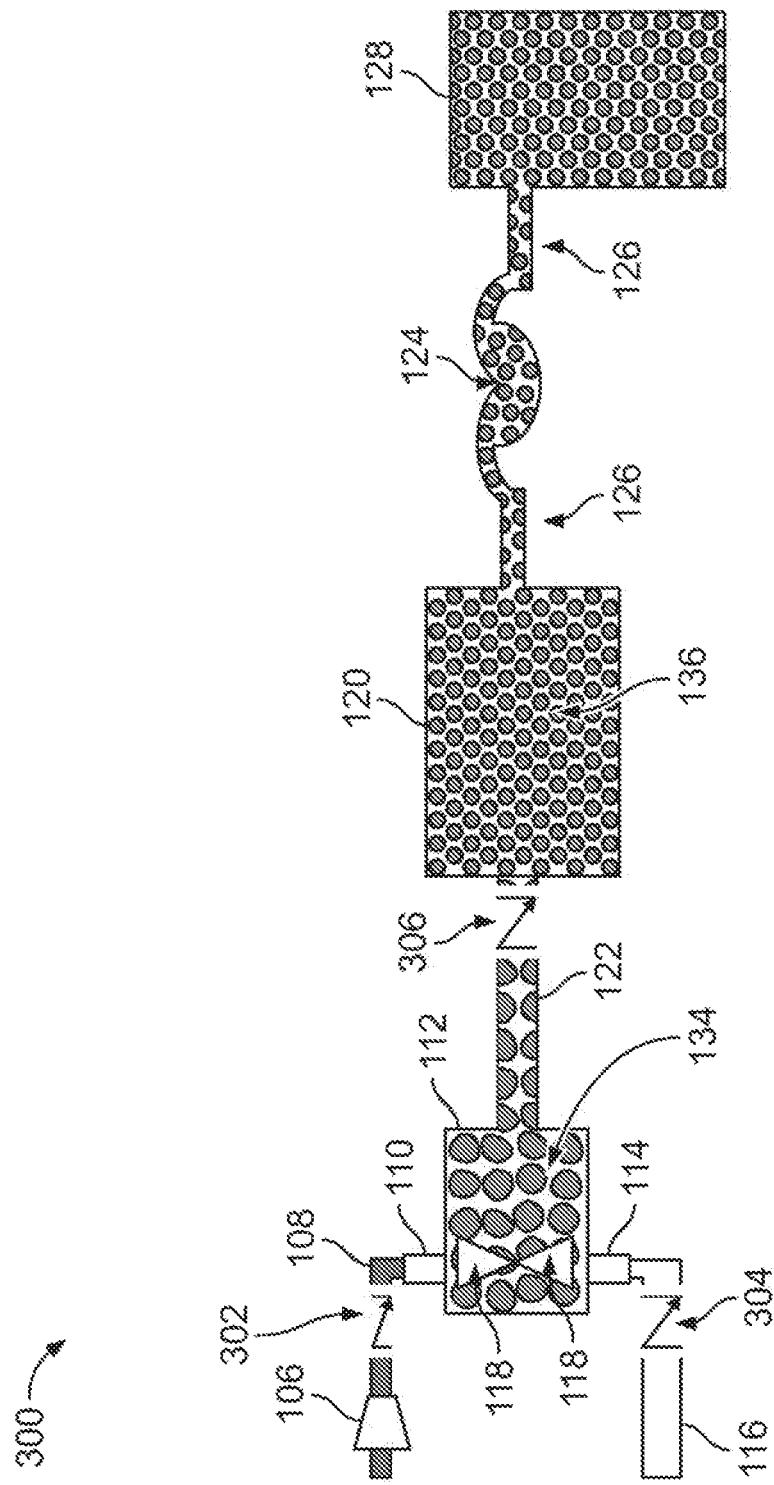
FIG. 3 shows a system for continuously processing at least two liquid feed streams in accordance with an embodiment of the present disclosure.

Referring now to FIG. 3, an illustrative system 300 for continuously processing at least two liquid feed streams in accordance with the present disclosure is schematically depicted. Pump 106 is connected to first port 110 of an in-line mixer 112 via first feed line 108. A check valve 302 is positioned on first feed line 108 between pump 106 and in-line mixer 112. Second feed line 116 is connected to second port 114 of in-line mixer 112. A check valve 304 is positioned on the second feed line 116 before the second port 114 of in-line mixer 112. In-line mixer 112 is connected to microreactor 120 via a conduit 122. A check valve 306 is positioned on conduit 122 between in-line mixer 112 and microreactor 120. Check valves 302, 304, and 306 are used to prevent backflow of the first liquid stream 130, the second liquid stream 132, and/or the substantially homogeneous mixture 134. In some embodiments, check valves 302, 304, and 306 are optional equipment.

Figure 4:
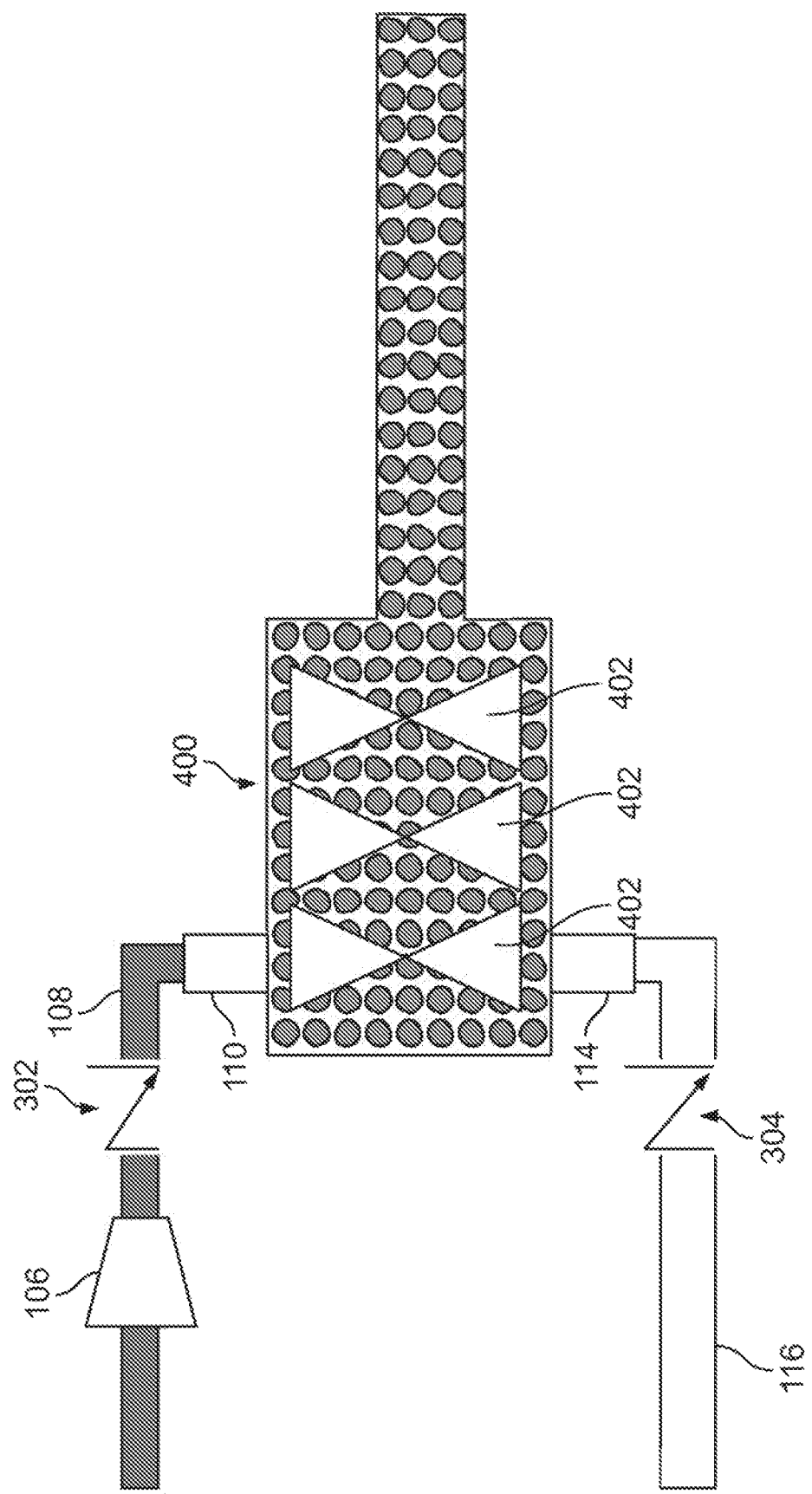
FIG. 4 shows an in-line mixer in accordance with an embodiment of the present disclosure.

Referring now to FIG. 4, an illustrative in-line mixer 400 in accordance with the present disclosure is schematically depicted. The in-line mixer 400 includes baffles 402. In some embodiments, the baffles 402 are employed in the in-line mixer 400 to increase the contact area for interaction between the first liquid stream 130 and the second liquid stream 132. In some embodiments, the baffles 402 are utilized to achieve desired hydrodynamic profiles, stress levels, and heat transfer as required by the system of the present disclosure.

Figure 5:
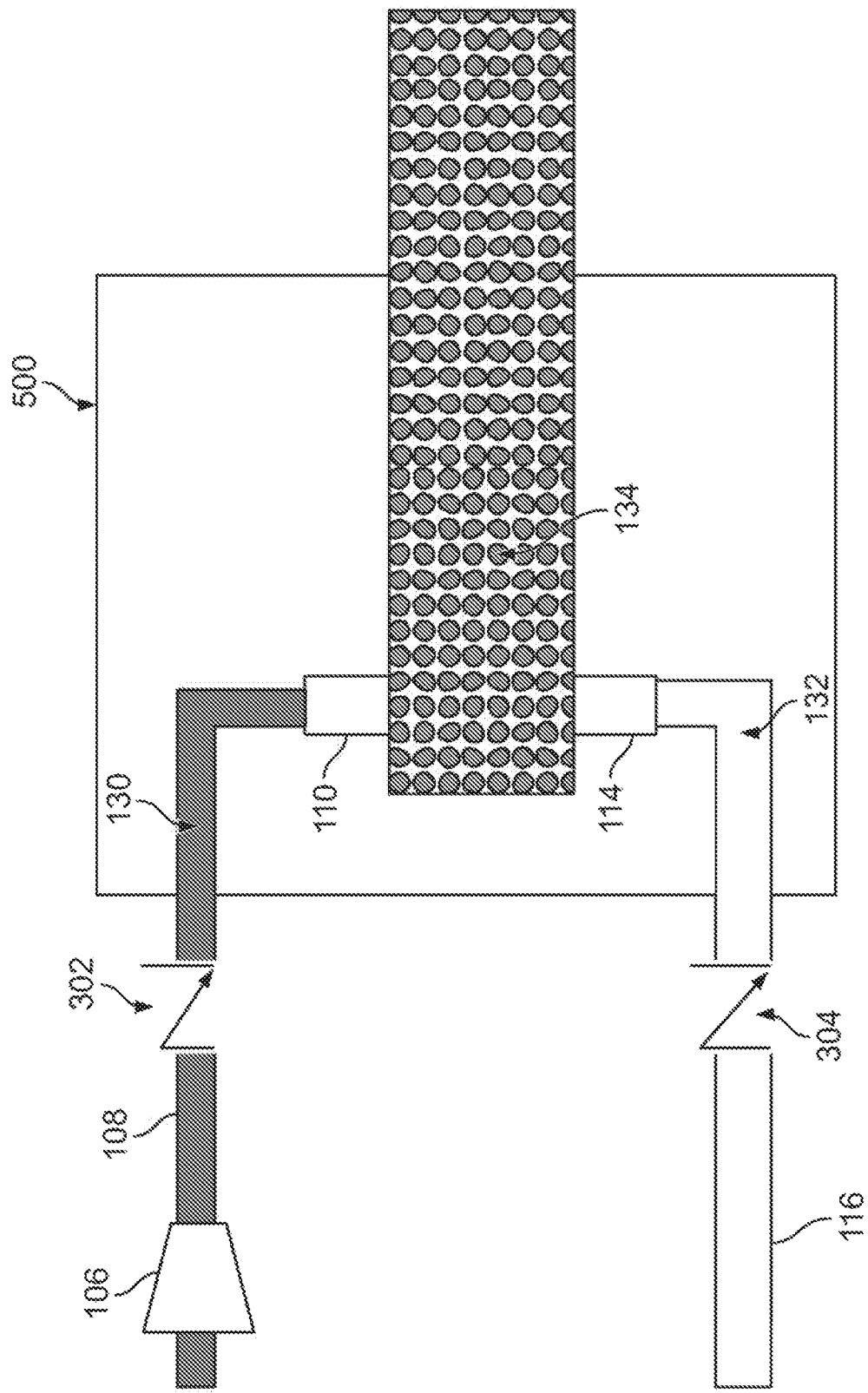
FIG. 5 shows an in-line mixer in accordance with an embodiment of the present disclosure.

Referring now to FIG. 5, an illustrative in-line mixer 500 in accordance with the present disclosure is schematically depicted. In-line mixer 500 is a T-mixer. First liquid stream 130 is pumped to first port 110 of the in-line mixer 500. Second liquid stream 132 flows to second port 114 of the in-line mixer 500. The first liquid stream 130 and second liquid stream 132 enter the in-line mixer 500 via the first port 110 and second port 114, respectively. In-line mixer 500 mixes the first liquid stream 130 and the second liquid stream 132 to form a substantially homogeneous mixture 134.

Figure 6:
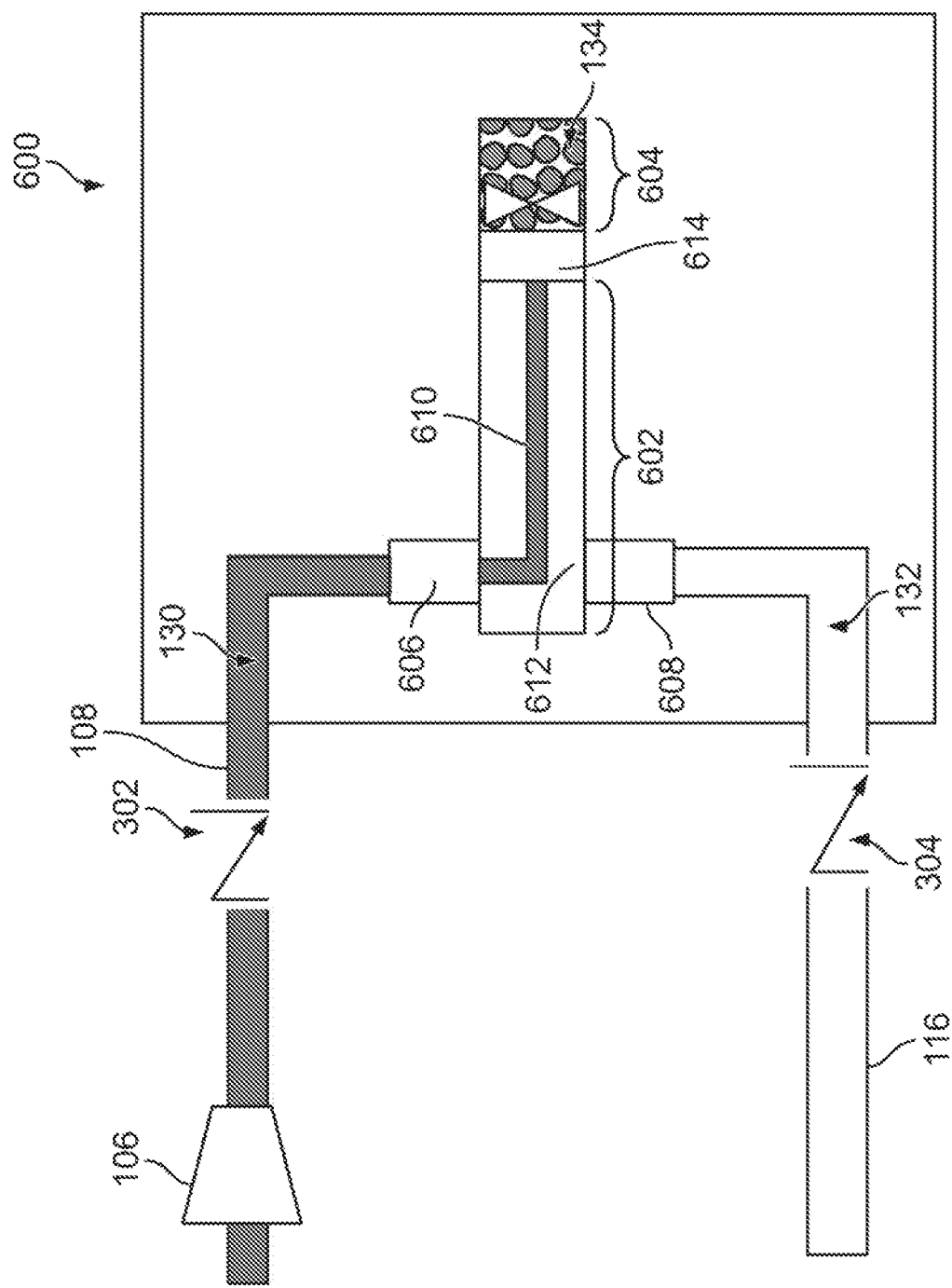
FIG. 6 shows a system for continuously processing at least two liquid feed streams in accordance with an embodiment of the present disclosure.

Referring now to FIG. 6, an illustrative system 600 for continuously processing at least two liquid feed streams in accordance with the present disclosure is schematically depicted. Pump 106 is connected to a first port 606 of a co-axial orifice 602 via the first feed line 108. The co-axial orifice 602 includes a first co-axial tube 610 and a second co-axial tube 612. The second feed line 116 is connected to a second port 608 of the co-axial orifice 602. First co-axial tube 610 and second co-axial tube 612 connects to third port 614 of the in-line mixer 604. In-line mixer 604 includes third port 614.

First liquid stream 130 is pumped to first port 606 of a co-axial orifice 602 via first feed line 108. Second liquid stream 132 flows to second port 608 of the co-axial orifice 602 via second feed line 116. The first liquid stream 130 and second liquid stream 132 enter the co-axial orifice 602 via the first port 606 and second port 608, respectively. The first liquid stream 130 enters first co-axial tube 610, and the second liquid stream 132 enters the second co-axial tube 612. While in the first co-axial tube 610 and second co-axial tube 612, first liquid stream 130 and second liquid stream 132, respectively, are flowing separately from each other. After first liquid stream 130 and second liquid stream 132 enter the in-line mixer 604 via third port 614, in-line mixer 604 mixes the first liquid stream 130 and the second liquid stream 132 to form a substantially homogeneous mixture 134. In comparison to the microreactor (not shown), in-line mixer 604 has lower energy levels by orders of magnitude.

In some embodiments, various components/equipment of the systems of the present disclosure may be controlled by a control system that includes a controller having one or more processors and one or more memory devices. In some embodiments, the one or more memory devices may include instructions stored therein that are executable by the one or more processors to control various functions and activities performed by the systems of the present disclosure.

Figure 7:
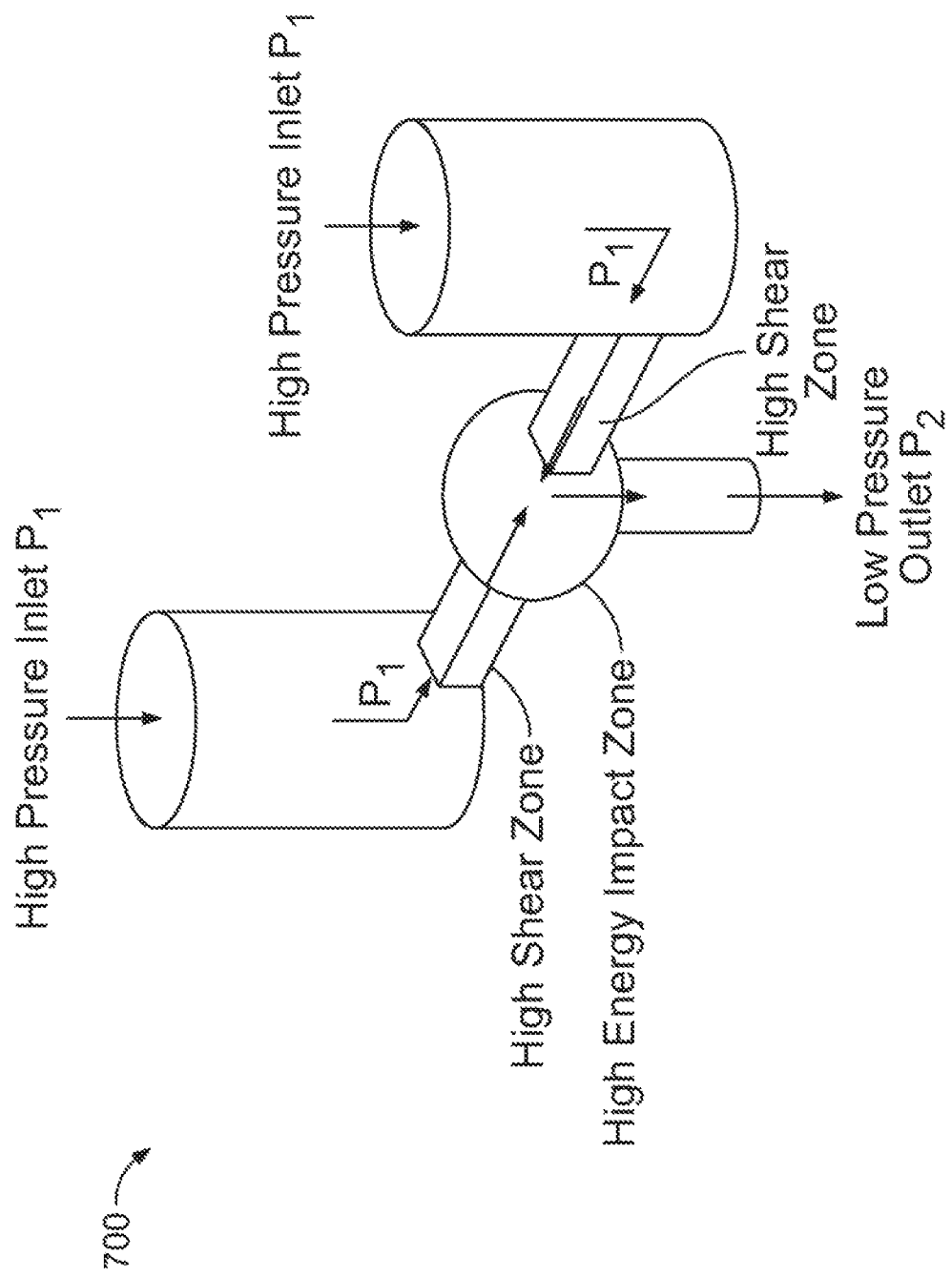
FIG. 7 shows a microreactor in accordance with an embodiment of the present disclosure.

Referring now to FIG. 7, an illustrative microreactor 700 in accordance with the present disclosure is schematically depicted. The microreactor 700 includes a pumping mechanism that generates high pressures, in the thousands or tens of thousands of psi. As used herein, the term "microreactor" is synonymous with "reaction chamber," "interaction chamber," and "processing module." The microreactor 700 also includes a processing module that contains passages with small dimensions, typically 10-5000 microns. There are a variety of pumping systems that may be utilized in microreactor 700, differing in the design and principal of operation. The geometry of the microreactor 700 may take various forms to effect the desired shear field and/or shear force. For example, the microreactor 700 may be characterized by (i) a "Z" or "L" type single slot geometry, (ii) a "Y" or "T" type single slot geometry, (iii) a "Z" or "L" type multi-slot geometry; or (iv) a "Y" or "T" type multi-slot geometry. The terms "Z" type and "Y" type refer to Microfluidics' reaction chamber geometries. The terms "L" type and "T" type refer to DyHydromatics' (Maynard, Mass.) reaction chamber geometries. Each of the foregoing microreactor geometries is known in the art and is generally adapted to provide a high shear field for interaction between the reactants/constituents introduced thereto. The microreactor 700 has an internal volume that is on the scale of a microliter, and average velocities in the microchannels may reach and/or exceed 500 m/s. Changes in velocity magnitude and/or direction associated with the microreactor 700 yields substantially uniform, high shear fields. The high turbulence achieved in the disclosed reaction chambers/microreactors advantageously facilitates mixing/contact at the nanometer level. The disclosed microreactor 700 is generally effective to generate nanoscale mixing, tight particle size distributions, and high levels of repeatability/scalability.

Fixed geometry homogenizers are known to produce materials with smaller particle size and narrower particle size distribution than the size of material produced with valve homogenizers. However, the contact times of fluids in valve homogenizers are generally shorter than those in fixed geometry homogenizers. Therefore, relatively fast processing may benefit from valve homogenizers in addition to minimizing the dimensions of the conduit between the in-line mixer and the homogenizer. The reason for this difference is the different pumping mechanism to produce high pressure that these homogenizers use. The fixed geometry homogenizers typically use constant pressure pumping mechanisms. These are plungers/intensifiers that first compress the fluid and then pump it through the processing module. Therefore, the flow through each intensifier is intermittent and the contact times of the fluids are relatively long. However, the valve homogenizers use constant volume pumping mechanisms. These are high pressure pumps and produce continuous flows through the homogenizers, and the resulting residence times are relatively short.

There are processing modules that enhance mixing of immiscible fluids while others enhance the shearing of solid particles. Additionally, there are processing module configurations that allow cavitation of the fluids while there are those that suppress cavitation. Therefore, for emulsions one may select processing modules that enhance the mixing of immiscible fluids. Processing module configurations that allow cavitation may be damaging to sensitive materials such as biologics; therefore, such configurations should be avoided in such applications.

Several parameters of the system can be controlled to produce tailored nanoparticles with desired properties according to some embodiments of the present disclosure, including, without limitation:

- The particle size of the substantially homogenous mixture depends on the turbulent energy dissipation rate (turbulent mixing intensity) of the in-line mixer. Each type of mixer has its own intrinsic rate, which may be further controlled by adjusting the operational parameters of the in-line mixer. Such operational parameters include the geometry of the in-line mixer and the flow rates of the individual liquid streams.
- The geometry of the conduit between the in-line mixer and the microreactor affects the contact time of the liquid streams. Slow processes require longer times and therefore longer conduits than faster processes.
- Additionally, the internal geometries of the in-line mixer and microreactor also affect the contact times.
- The microreactor highly influences the final particle size through (i) the pressure, which is a measure of the energy imparted on the fluid, and (ii) the geometry of the processing module of the microreactor. The processing module of the microreactor has various names, depending on the type of the device and the manufacturer. For example, in valve homogenizers the processing module is named a homogenizing valve. Microfluidics names its processing modules interaction chambers while DyHydromatics names their processing modules reaction chambers. Another name commonly used to describe the processing module is a microreactor.
- The temperature of the fluids throughout the system influences the final product.

The types of materials that can be produced by the apparatus, systems, and methods of the present disclosure include nanoemulsions, nanodispersions, liposomes (semi-solids), lipid nanoparticles (semi-solids), crystalline or amorphous materials, complex particles with ingredients embedded in a solid, semi-solid or liquid matrix, complex particles with ingredients encapsulated by solid, semi-solid or liquid materials, polymer particles, and high purity chemicals (not necessarily containing particles), to name a few. Such materials are generally produced by creating two liquid phases and mixing the phases together. In some embodiments, the phases are miscible. In some embodiments, the phases are immiscible. In embodiments including mostly hydrophobic or mostly hydrophilic constituents, the phases are referred to as the "oil phase" and the "water phase."

In some embodiments, the oil phase may contain an oil phase constituent selected from vegetable oil (including, without limitation, soybean oil, olive oil, palm oil, corn oil, canola oil, sesame oil, rice oil, refined vegetable oils, oils rich in omega-3 fatty acids, and algal oil), nut oils, animal oils (including, without limitation, fish oil), inorganic oils (including, without limitation, mineral oil, perfluorocarbon oils including, without limitation, FC43, and perfluorodecalin), lipids (including, without limitation, egg phospholipids, lecithin, phosphatidylcholine, cholesterol, Palmitoyl oleoyl phosphatidylcholine, cationic lipids, and anionic lipids), modified or functionalized lipids (Hydrogenated phosphatidyl choline from soybean lecithin, N-(Methylpolyoxyethylene oxycarbonyl)-1,2-distearoyl-sn-glycero-3-phosphoethanolamine, and sodium salt (DSPE-PEG)), waxes (including, without limitation, beeswax, and paraffin wax), surfactants (including, without limitation, Tween®, Span®, poloxamers such as 188, Solutol® such as polyethylene glycol (15)-hydroxystearate, block co-polymers), polymers (including, without limitation, poly lactic acid (PLA), poly lactide-co-glycolide (PLGA), poly-epsilon-caprolactone, poly styrene, acrylics such as poly methyl methacrylate, crosslinked polymers, alginates, and mixtures of polymers), active ingredients (including, without limitation, pharmaceutical, nutraceutical, cosmeceutical, small molecules, proteins, peptides, RNA and DNA, anti-oxidants such as vitamin E and K, cannabis products (CBD/THC), cancer therapeutics, anesthetics, ocular drugs, antibiotics, and inhalable drugs), flavorings and colorings (natural or synthetic flavoring oils), alcohols (including, without limitation, ethanol, methanol, benzyl alcohol, ethylene glycol, and propanol), organic solvents (including, without limitation, acetone, DMSO, alcohols, ethyl acetate, ethylene chloride, hexane, toluene, and polyethylene glycols of various molecular weights), and/or derivatives of any of the foregoing constituents including, without limitation, fluorinated, pegylated brominated, and hydrogenated.

In some embodiments, the water phase may contain a water phase constituent selected from water, lipids (including, without limitation, egg phospholipids, lecithin, phosphatidylcholine, cholesterol, Palmitoyl oleoyl phosphatidylcholine, sterols, neutral lipids, cationic lipids, and anionic lipids), modified or functionalized lipids (including, without limitation, hydrogenated phosphatidyl choline from soybean lecithin, N-(Methylpolyoxyethylene oxycarbonyl)-1,2-distearoyl-sn-glycero-3-phosphoethanolamine, and sodium salt (DSPE-PEG)), surfactants (including, without limitation, Tween®, Span®, poloxamers such as 188 and 407, Solutol® such as Polyethylene glycol (15)-hydroxystearate, block co-polymers, polysaccharides, casein, lecithin, whey protein, gelatin, mono- and di-glycerides, derivatives such as acetylated, succinylated and diacetylated tartaric esters of distilled monoglycerides, lactylated esters, sorbitan esters, polysorbates, propylene glycol esters, sucrose esters, and polyglycerol esters), viscosity modifiers (including, without limitation, glycerol), pH adjusters (including, without limitation, sodium hydroxide, sodium phosphate, potassium phosphate, sodium oleate, citric acid, hydrochloric acid, nitric acid, acetic acid, and buffers), and sugars (including, without limitation, sucrose, fructose, polysaccharides, and starches).

Each of the disclosed system designs may be advantageously employed according to the present disclosure to achieve variable/desired ratios between feed streams within the downstream microreactor.

B. Exemplary Process Implementations

The disclosed apparatus/system may be used in a wide range of applications and/or implementations, e.g., particle size reduction applications (e.g., emulsion and suspension applications), cell disruption application (e.g., *E-coli* and yeast applications), and reaction applications (e.g., crystallization applications). Several exemplary applications/implementations are described herein below. However, such exemplary applications/implementations are merely illustrative, and are not limiting with respect to the scope of the present disclosure.

Before describing specific exemplary implementations of the present disclosure by way of "examples" herein below, several broad principles having applicability to the disclosed apparatus/systems and their application are described. These broad principles may be employed to identify, evaluate, implement and/or enhance operations according to the present disclosure.

(1) Physical Processes

Examples of physical processes that may be facilitated and/or supported according to the present disclosure include crystallization processes, precipitation processes, emulsion formation processes, particle coating processes, and particle mixing processes. The foregoing processes generally benefit from molecular interaction at the nanometer scale. Each of these processes can be undertaken using the disclosed apparatus/systems according to different methods and/or roadmaps (i.e., processing of specific constituents under specific process parameters to achieve specific results), as will be readily apparent to persons skilled in the art. For example, processing a solvent and antisolvent stream (and optionally a surfactant) with the disclosed apparatus/system may lead to crystallization or precipitation of the solute dissolved in the solvent stream. Similarly, changing the pH of a solution by mixing the initial solution with a stream that changes the pH of the final solution may result in crystallization and/or precipitation of the solute.

In addition, emulsions may be formed by direct and continuous interaction of continuous and dispersed phases, e.g., an oil stream with an aqueous/water stream. Typically, stable emulsions and nano-emulsions are formed in two steps. Initially, a coarse pre-emulsion is made by mixing the immiscible liquids with conventional mixing equipment, such as a propeller or a rotor/stator mixer. Subsequently, in some embodiments, the coarse emulsion may be processed using a standard MICROFLUIDIZER® processor (Microfluidics Corp., Newton, Mass.) or a high shear homogenizer. However, with the disclosed apparatus/system, the step of producing pre-emulsions may be advantageously avoided.

Further, coating of solid particles can be achieved according to the present disclosure by interacting liquid suspensions of solid particles with a solution containing the desired coating material(s). Coatings can thus be formed by physical or chemical adsorption of the coating material onto the particle surface.

(2) Chemical Processes (Chemical Reactions)

Chemical reactions of single or multiphase liquids can be enabled and/or expedited according to the present disclosure, e.g., when reactant streams are forced to interact inside the fixed, small volume geometry of a reaction chamber/microreactor. Flow through the reaction chamber/microreactor advantageously increases the interaction surface area among the reactant streams to a significant degree, thereby minimizing potential diffusion limitations and increasing reaction rates. Undesirable side reactions and/or slow reactions can be minimized by creating conditions within the disclosed reaction chamber/microreactor, wherein the conditions are analogous to a "well stirred reactor". Indeed, the disclosed apparatus/systems may be effective in avoiding reactions that are a result of concentration gradients.

Exemplary chemical reaction categories that are supported by the disclosed apparatus/systems include, without limitation, acid-base reactions, ion exchange processes, reduction/oxidation reactions, polymerization reactions, precipitation reactions, substitution reactions, crosslinking reactions, reactive crystallization reactions, biodiesel reactions, and the like. More particularly, the following exemplary application/implementation categories may benefit from processing with the disclosed apparatus/system: (i) production of nanoparticles via crystallization, precipitation or chemical reactions; (ii) coating of particles; (iii) mixing of heterogeneous materials at the nanometer scale; (iv) expediting chemical reactions, and (v) Process Intensification

C. Performance Enhancement

According to testing performed according to the present disclosure, mixing intensity may be identified from estimates of the length scales associated with turbulent eddies (and thus Kolmogorov diffusion lengths) in the nanometer range. Time scales for the macro-, meso-, and micro-mixing processes may thus be estimated and, along with the length scales, prediction of operational roadmaps may be undertaken that correlate well with transport rates, particle size observations, and well established theoretical approaches. Such testing permits enhancement of system performance, such that the disclosed apparatus, systems and methods may be effectively and advantageously used, inter alia, to measure millisecond kinetics, conduct micro-scale reactions, facilitate formation of nano-emulsions/suspensions via turbulent mixing, and achieve enhanced mass transfer operations needed for controlled nucleation and growth in precipitation and crystallization, e.g., for protein and inorganic substances.

Representative values for system parameters according to exemplary implementations and/or applications of the present disclosure are as follows:
 reaction chamber residence times from 0.5-1 ms;
 micro-mixing time scales of 1-4 $\mu$s;
 turbulent energy dissipation rates on the order $10^7$-$10^8$ W/kg;
 nano-emulsion droplet and particle diameters in the range 25-500 nm:
 diffusion coefficients from $1$-$5 \times 10^{-9}$ m2/s; and
 interface transfer coefficients as high as 0.5 m/s.
 Chemical conversion and pathway selectivity of 100% can be advantageously demonstrated according to exemplary implementations of the present disclosure.

As a general principle, process intensification (PI) facilitates integration of operational steps within a smaller number of scale-reduction vessels, thereby supporting miniaturization of unit operations and processes. In situ separation schemes within continuous flow micro-reactors are classic examples. Adaptation of PI strategies based on the present disclosure provides numerous benefits. Exemplary advantageous outcomes that may be realized through adaptation of the disclosed PI strategies include:
 High throughput with higher product purity and uniformity;
 Efficient start-up and shut-down procedures, which translates to, inter alia, reduced inventory/surge systems and reduced "off-specification" material;
 Decreased expenditures, which translates to, inter alia, low/reduced capital costs, lower energy use and reductions in other operating costs, and reduced space requirements/smaller plant footprint;
 Enhanced operability and control;
 Environmental advantages and/or pollution prevention;
 Lower plant profile; and
 Safety benefits, which translate to, inter alia, decreased volumes of explosive, hazardous or toxic compounds, enhanced operator friendliness, and potential isolation in secondary containment chambers, as desired.

The apparatus/systems and methods of the present disclosure facilitate improved reactor performance. In particular, the disclosed reactors can provide a number of key advantages by, for example, cutting residence times, accelerating reaction rate, minimizing side reactions and/or reducing energy intensive downstream processing steps, such as distillation and extraction. With many reactions, there are significant heat and mass transfer limitations which are determined by the contacting patterns obtained via the intensity of mixing (i.e., the hydrodynamics). These heat/mass transfer limitations can thus control the observed system dynamics, rather than fundamental kinetics of the reaction system.

Depending on reaction dynamics of a particular system, there are several ways that apparent reaction rate of a particular system can be increased according to the present disclosure. For example, mass transfer limitations that are common to heterogeneous reactions may be removed by increasing the surface area-to-volume ratio of the dispersed phase. Once the mass transfer limitations are removed (or substantially reduced), the reaction may advantageously proceed according to the intrinsic kinetics.

As a further example, enhanced identification and/or control of the temperature profile throughout the reactor may be achieved, which generally leads to better control of the reaction rate. By way of illustration, a highly exothermic reaction carried out in a large batch vessel may require several hours, not because of any inherent kinetics constraint but because of the time necessary to remove the heat of reaction safely via its poor transfer area-to-volume ratio using a traditional coil configuration. With intense mixing and improved heat transfer mechanisms associated with the low holdup of material in the reactor, better productivity is possible according to the present disclosure. As a result of these enhanced transport capabilities/features, the selectivity of a multiple reaction scheme increases, resulting in improved product yields and quality with reduced separation requirements.

Process data, connected with computational fluid dynamics (CFD) modeling, may advantageously provide a basis for design, redesign and/or reconfiguration of system designs and layouts. CFD can also be used to predict: (1) velocity and stress distribution maps in complex reactor performance studies; (2) transport properties for non-ideal interfaces; and (3) materials processing capabilities useful in encapsulation technology and designing functional surfaces, especially where self-assembly mechanisms, surface tension and interfacial forces, and turbulent energy driven processes dominate.

D. Precipitation and Crystallization Processes

Both precipitation and crystallization processes are characterized by a solid material that is formed from solution. Such processing schemes are widely used in production of pharmaceutically active ingredients, proteins and other chemical products. The main difference in these two processes is that precipitation produces a solid of poorly defined morphology, whereas crystals grow with a well-defined 3-dimensional lattice structure. Typically, the primary objectives for both precipitation and crystallization processes are to (1) increase concentration, e.g., when precipitating from a dilute solution, and/or (2) purify a material, such as when selectively crystallizing one species from a solution containing multiple types.

Each process is generally initiated by changes in the thermodynamic state of the solution, thereby reducing the solubility of the target species. Initiation may thus be undertaken via temperature adjustment(s), concentration adjustment(s), e.g., by addition of antisolvents, or adjustment of solution activity coefficients, e.g., by addition of ionic species. As an example, when dealing with solubility of proteins, processing approaches may include: (1) pH adjustment to the isoelectric point, (2) addition of organic solvents, (3) increasing ionic strength to cause salting out, and/or (4) addition of non-ionic polymers.

Nucleation sites must be created to initiate precipitation and/or crystallization processes, either by generating a very high super-saturation resulting in spontaneous growth (homogeneous nucleation) or seeding the solution with surfaces for growth (heterogeneous nucleation), whether inert or the desired target species. In all cases, it is essential that the solubility of the target species be reduced below the actual concentration in solution. This effectively creates a concentration in excess of the thermodynamic equilibrium saturation value and rate processes then dominate system behavior. The magnitude of the difference from equilibrium, i.e., degree of super-saturation, influences both type and rate of system response.

Precipitation conditions are often obtained via chemical reactions producing species with limited solubility in the reaction mixture. This is one method of generating the local high degrees of super-saturation required for desired rapid kinetics. The process occurs in four serial, but often overlapping, steps:

(1) The feed solution and reagent are mixed. The time required to achieve homogeneity is generally dependent on diffusivity of the target species and distance the target species molecules must travel within the mixing eddies (i.e., Kolmogorov length), which can be estimated using turbulence theory. Calculation/analysis requires knowledge of the mixing power input and subsequent energy dissipation rate per unit volume along with solution properties such as density and viscosity.

(2) Subsequent to the mixing step which is aimed at obtaining a desired degree of super-saturation, nucleation of small solid particles occurs. The nucleation rate increases exponentially with respect to super-saturation up to a characteristic limiting rate, and the features of the product formed depend significantly on this rate. If the nucleation rate is too high, the result is likely to be a colloid (i.e., highly solvated) and, thus, complicated downstream processing may be required.

(3) Growth rate is determined by diffusion of solute molecules from the bulk solution to the solid surface and/or a surface integration rate, until a limiting particle size is reached. The limiting particle size is generally determined by the magnitude of shear in the mixed solution.

(4) Once the limiting particle size is reached, further growth is by flocculation, whereby particles collide and adhere to each other. Particle number thus decreases with time exponentially as the particle size increases. Finally, as the particles grow in size, the shear forces in the mixed solution cause fracture; resulting in a size plateau at long mixing times.

Thus, important parameters in a precipitation process are (a) degree of super-saturation achieved in the initial mixing, which is dependent upon reagent volume, and (b) shear stress in the mixed solution, which is proportional to power input per unit volume of solution.

Like precipitation, the crystallization process begins by reducing the solubility of the target species. However, relatively low degrees of super-saturation are utilized since, at high levels, the solids formed tend to be an amorphous precipitate (rather than crystalline). Control of the rate processes, as discussed above, is essential to directing the path to a desired final thermodynamic state and to achieving a desired morphology. Spontaneous formation of solids can entrap undesired species into the lattice framework. Thus, slowing the growth rate by reducing/lowering the super-saturation level permits higher selectivity in the surface integration mechanism, i.e., crystals are formed that are very pure due to exclusion of other contaminate species. Locally high shear forces can also help maintain appropriate/desirable transport gradients. Crystallization may thus be used as a primary separation method and/or as a finishing step to yield product of desired purity according to the present disclosure.

E. Nano-Encapsulation

The ability to form nanoscale particles and/or emulsions that encapsulate active ingredients has applicability in many facets of the engineering biosciences. For example, nano-technologies are having a major impact on drug delivery, molecular targeting, medical imaging and biosensor development, as well as on cosmetic and personal care products, and nutraceutics. Unfortunately, conventional mixing equipment in which a high shear, elongated flow field is generated near the tip of high-speed blade(s) only generate emulsions with droplet sizes in the range 500 nm and larger. Such emulsions are stable only if sufficient surface active agents are present to control agglomeration and re-growth. This approach to emulsion stability requires proper distribution of the surfactant for the appropriate surface coverage of the droplets, thereby minimizing Oswalt ripening and subsequent undesired size distribution changes. The higher shear rates achieved according to the present disclosure advantageously facilitate generation of stable mean particle sizes in the range 50 to 100 nm and requisite/desired narrow particle size distributions. The disclosed systems/techniques may also advantageously dispense with the need for surfactants for stability, dependent upon the surface characteristics of the emulsion constituents and their intended applications.

F. Creating Nano-Scale Particles/Entities

High shear fields have been developed in the reaction chambers/microreactors of the present disclosure to produce particles with diameters in the range 50 to 100 nm. Such particles are about the size of the smallest turbulent eddies generated in such processing units. For example, jet impingement on a solid surface (e.g. Z-type microreactor) or with another jet (e.g., Y-type microreactor) has been shown to be highly efficient. Systems that incorporate high velocity linear fluid jets that collide can rapidly reduce the scale of segregation between the streams. These jets can be considered as free, submerged, or confined. A free jet stream is not affected by the walls of a surrounding chamber/vessel nor any surrounding fluid, in contrast to submerged jets where viscous drag forces may be significant. With confined impinging jets, the dimensions of the chamber/vessel relative to jet diameter can play a major role in system performance.

The importance of chamber/vessel dimensions relative to jet diameter is apparent from the micro-mixing time and its relative magnitude compared to the process characteristic time in such jet-based systems. To minimize process sensitivity to mixing, it is generally necessary to reduce the mixing time constant (including macro-, meso-, and micro-mixing) to a fraction of the most significant/relevant process time constant. Length scales are typically used to classify mixing processes, i.e., macro-mixing occurs at vessel dimension scale, meso-mixing is at the turbulent eddy scale, and micro-mixing is on the scale of molecular diffusion in stretching fluid lamellae.

According to apparatus/systems of the present disclosure, high-energy dissipation is observed in the disclosed microreactor designs because the kinetic energy of each stream is converted into a turbulent like motion as the result of the collision and redirection of the flow, e.g., within the very small volume defined by the reaction chamber/microreactor, and the associated shear forces. The size of virtual cylindrical volume elements of exemplary microreactors of the present disclosure may be quantified using computational fluid dynamics (CFD) techniques and has been calculated to be on the order of seven (7) to ten (10) jet diameters for the radial dimension of the impingement plane. The other cylinder dimension (height) has been shown to be independent of jet diameter and the design thereof is typically related to the inter-penetration length of the two jets. In exemplary embodiments of the present disclosure, the height dimension is calculated to be about 10 percent of the inter-nozzle (jet separation) distance.

Interfacial mass transfer area may be used to characterize mixing quality and to quantify associated length scales. Using known transfer areas, diffusion lengths, and physico-chemical properties of fluids that permit measurement of appropriate rate phenomena to determine transport parameters, it is possible to determine an interfacial transfer coefficient, mass diffusivity, and a system characteristic time constant. Connecting these fundamental parameters with system geometric configurations, operating variables and measured performance metrics (such as quantity transported and approach to equilibrium, if not obtained), it is possible to determine transfer areas that must necessarily be present in an reaction chamber/microreactor. In addition, from this interfacial area, it is possible to identify the eddy size scale (i.e., Kolmogorov diffusion length). Consequently, a measure of mixing intensity can be obtained which provides a basis for predicting and/or achieving desired average droplet sizes when generating nano-emulsions and other dispersed systems.

G. Flow Patterns, Mixing and Transport Phenomena

As is readily apparent, it is important to design systems with appropriate hydrodynamic characteristics with respect to transport phenomena and effects on dynamic response (whether chemical reaction kinetics or other rate processes). Beyond system design, process innovations are disclosed herein that (i) utilize flow instabilities for mixing, (ii) improve contacting patterns to enhance interactions that promote better kinetics performance and transport rates, and (iii) improve transport via mechanical turbulence promoters.

Description of Process and Controls for a Method for Continuously Processing at Least Two Liquid Feed Streams

A. Process

The process has the following steps:

1. Determining the Volume Factions of Each of the Liquid Streams

This step generally starts with the desired formulation of the final product at each stage of processing. The examples below show how to set up the system of the present disclosure to create an emulsion from two immiscible liquid streams. This similar procedure is used when mixing miscible liquid streams for the purpose of conducting crystallization, precipitation, and chemical reactions, among others.

Option 1. In this option, an oil/water emulsion in which the oil phase is 5% by volume and the water phase is 95% by volume is created. The volume fraction of the oil phase of the emulsion in the final formulation is 5/100=0.05 while the fraction of the water phase is 95/100=0.95. The ratio of the two streams, water to oil, is 0.95/0.05=19. During processing, this ratio must stay constant at this ratio value or deviate little from this ratio value to achieve a final formulation with the desired composition.

Option 2. The desired formulation of the final product may be different than the formulation at intermediate stages. In Option 1, it is possible that the oil phase is delivered in two steps. For example, in the first step, half of the oil is delivered to the water phase to create an emulsion with 2.5% by volume oil. In the second step, this first emulsion becomes one of the streams, while the other stream consists the remainder of the oil. The ratio of the water to the oil in the first emulsion is 0.975/0.025=39. The volume ratio of the first emulsion to the second (and final) oil stream is 100/0.025=40.

Option 3. It is possible that a concentrated emulsion is homogenized. After homogenization, the concentrated emulsion may be diluted further with addition of the continuous (water) phase or parts of the water phase. In Option 2, it may be possible to homogenize an emulsion containing 10 vol % oil without sacrificing the particle size. This emulsion is then diluted with the addition of the water phase or pure water such that the final concentration of the oil phase in the emulsion is 5 vol %.

B. Flowrate Calibration

The flow rate of each stream is calculated as follows.

The total flow rate of the system of the present disclosure is measured at the outlet of the homogenizer. Subsequently, each of the metering pumps is set to provide the appropriate flow rate based on the desired volume fraction of the particular stream in the final formulation. The total flow rate of the homogenizer is measured under set conditions of pressure, hardware, type of in-line mixer upstream, and temperature when a single stream of the material is processed. The flow rate of each of the streams is calculated by multiplying the total flow rate with the percentage of that stream in the formulation, the final or intermediate, based on the specific formulation.

In Option 1 of the previous section, to produce a 5% by volume oil-in-water emulsion when the total flow rate is 300 ml/min, the oil metering pump (if present) should be set at 15 ml/min (5% of 300 ml/min) while the water metering pump (if present) should be set at 285 ml/min (85% of 300 ml/min). The flow rate of the input streams not having a dedicated metering pump may be controlled indirectly by the pumping action of the homogenizer.

There may be hardware configurations that have a metering pump for each input liquid stream. Such configurations are in addition to an optional main pump that feeds the homogenizer, which is located downstream of the metering pump, as shown in FIG. 1.

Finally, there may be hardware configurations which do not have a main feed pump for the homogenizer because the homogenizer is self-fed. The flows in this configuration can be calibrated as described above.

The accuracy of the calibration may be optionally verified by conducting analytical testing on the final formulation to verify that the final composition is within the acceptable range.

2. Homogenization 2.1 Priming

Priming is completed to remove air from the system of the present disclosure, which, in some embodiments, includes the metering pump(s), the in-line mixer, the feed pump(s), the homogenizer, and the lines connecting those. Priming is accomplished by passing a liquid through the system generally at a low pressure. Optionally, priming is sometimes completed using the stream with the highest flow rate or the stream with constituents that are readily available or inexpensive.

2.2 Processing

Once the homogenizer is primed, the pressure is set to the desired value and the pump of the second stream is turned on. The initial volume equal to the holdup volume of the machine is discarded because it does not contain ingredients from the second stream.

Once the homogenizer is set at the correct pressure and the initial material is discarded, the homogenizer produces the material with the desired composition. Following the first pass of the liquid streams through the homogenizer, there may be several other processes depending on the outcome of the first pass.

It is possible that the first pass through the homogenizer does not result in the desired product quality in terms of particle size or composition. In this case, further processing steps may be required as follows:

(a) If the composition of the formulation is similar to the desired formulation but the particle size is larger than desired, the material is processed through the homogenizer a few more times, if necessary, until the desired particle size is achieved. In this case, after the first pass, a single liquid stream will be processed each time through the homogenizer.

(b) If the composition of the formulation is incorrect because, for example, only part of the one liquid stream had been incorporated in the preliminary formulation, the remaining material may be incorporated in a similar method during a second pass through the homogenizer. In this case, for example, the end formulation from the first pass may constitute one of the streams in the second pass.

(c) A combination of (a) and (b) may be required in some embodiments.

3. Dilution

If the final concentration is higher than that desired, dilution may be appropriate.

4. Quenching

Quenching is used to stop processes from continuing. For example, quenching may be used to stop a chemical reaction and/or crystal growth during crystallization, to prevent oil droplets from coalescing with each other, and/or to prevent particles from agglomerating, among others.

5. Aseptic Filtration

6. Lyophilization

C. Controls

1. Flowrate Ratio Control

It is possible to control the flow rate ratio in real time or at a certain frequency during operation. This is conducted by first measuring either directly or indirectly the total flow rate of the system at the end of the homogenizer at a certain frequency, and then adjusting the flow rate of each stream based on the desired flow rate ratio of each stream.

Figure 8:
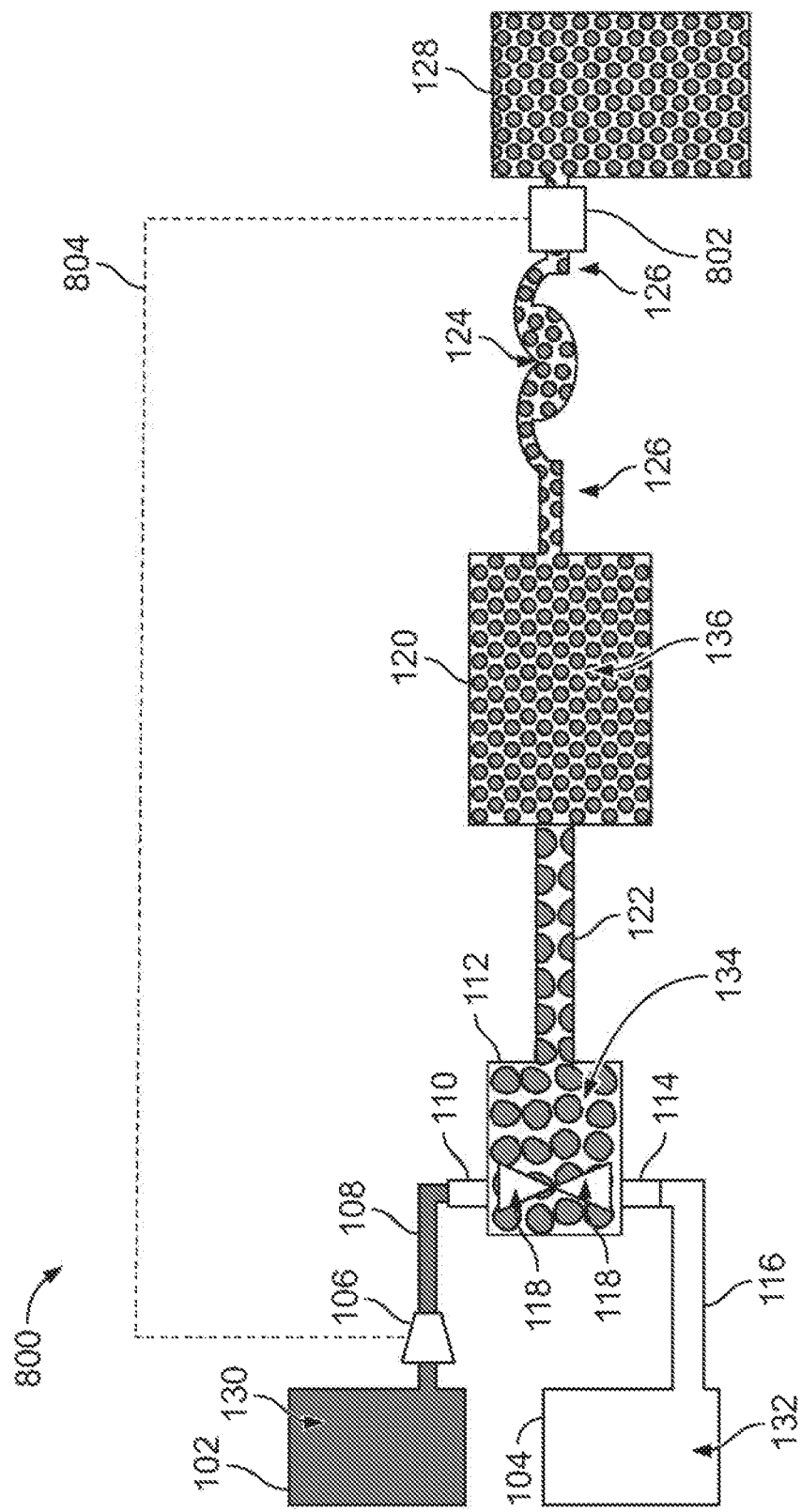
FIG. 8 shows a system for continuously processing at least two liquid feed streams in accordance with an embodiment of the present disclosure.

Referring now to FIG. 8, an illustrative system 800 for continuously processing at least two liquid feed streams in accordance with the present disclosure is schematically depicted. A flowmeter 802 is positioned on conduit 126 in between heat exchange unit 124 and collection tank 128. Flowmeter 802 measures the total flow rate of the system 800. Direct measurements of the flow rate ratio may be conducted with the use of flowmeter 802. In some embodiments, gravimetric measurements may be performed. Indirect measurements may be conducted by counting the stroke rate of the microreactor 120. In embodiments in which the microreactor 120 is a constant pressure homogenizer, such homogenizers typically deliver a constant liquid volume per stroke. In some embodiments, an electronic signal, which is related to the magnitude of the flow rate (input signal), may be generated. Based on the input signal, output electronic signal(s) 804 may be generated by flowmeter 802 and delivered to pump 106. In some embodiments, output electronic signal(s) 804 are delivered to pump 106 via electrical wiring (not shown) or wirelessly (not shown). Output electronic signal(s) 804 may be estimated to represent the desired flow rate of each stream. Output electronic signal(s) 804 are used to control the flow rate of pump 106. In some embodiments, the output electronic signal(s) 804 control of pump 106 occurs in real time. In some embodiments (not shown), output electronic signal(s) 804 are used to control the flow rate of valves (not shown).

2. Emergency Stop

Figure 9:
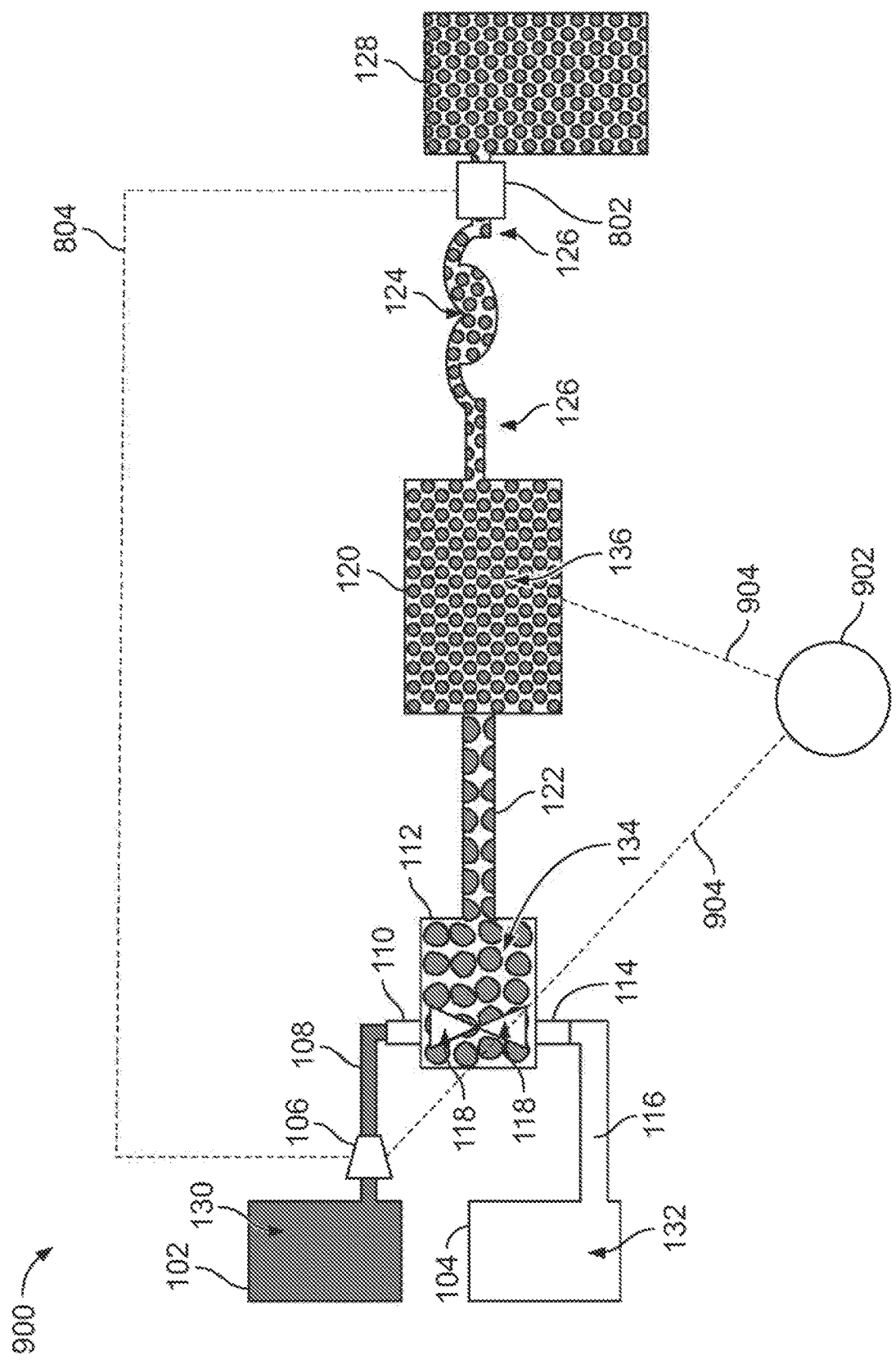
FIG. 9 shows a system for continuously processing at least two liquid feed streams in accordance with an embodiment of the present disclosure.

Referring now to FIG. 9, an illustrative system 900 for continuously processing at least two liquid feed streams in accordance with the present disclosure is schematically depicted. Emergency Stop (E-Stop) 902 is electrically connected to microreactor 120 and pump 106. In some embodiments, E-Stop 902 is electrically connected to microreactor 120 and pump 106 via electrical wiring or wirelessly. E-Stop 902 is electrically connected to a switch 904. Pump 106 and microreactor 120 are electronically connected to E-Stop 902. In some embodiments, E-Stop 902 is connected to any suitable equipment used in system 900.

The E-Stop 902 is utilized to stop all key equipment in system 900 at the same time in case of an emergency. If the microreactor 120 stops while the pump 106 is operating, it is possible that the feed lines are over pressurized or expensive material may be leaking or otherwise wasted. The E-Stop 902 is designed such that when the microreactor 902 stops, the E-Stop 902 forces the pump 106 to stop. Additionally, if the microreactor 120 is slowing down or speeding up due to blockage or loss of liquid streams, respectively, the pump 106 is forced to stop.

In some embodiments, a single E-Stop 902 is utilized for the pump 106, the microreactor 120, automated valves (not shown), and other upstream and downstream pieces of equipment (not shown). Switch 904 is utilized in system 900 to turn off the power to any equipment that is connected to the E-Stop 902.

EXAMPLES

The following non-limiting examples illustrate certain advantages and improvements of the apparatus/systems and methods for continuously processing at least two liquid feed streams according to some embodiments of the present disclosure. These examples are meant to be illustrative only and are not intended to limit or preclude other embodiments of the present disclosure.

Example 1

Oil/Water Emulsion Using the Dual Feed Emulsification Method

The formulation by weight and by volume shown in Table 1 is prepared.

TABLE 1

| | Batch Size | |
|---|---|---|
| | 100 g (g) | 100 ml (ml) |
| Mineral oil | 37.00 | 44.58 |
| Tween 80 | 2.40 | |
| Water | 60.60 | 55.42 |

The water (60.60 g) is heated in a beaker on a hot plate to 55° C. Tween® 80 (2.40 g) is added to the water while the mixture is stirred constantly with a magnetic stirrer until the Tween® 80 is completely dissolved. The mineral oil is also heated to 55° C.

After 1-2 minutes, the oil is poured into the water while the mixture is homogenized using a rotor-stator mixer (T25 Ultra Turrax, IKA) that is rotating at 20,000 rpm. After a total mixing time of 5 minutes, a coarse emulsion is poured into the reservoir of a HP350-30 high-pressure homogenizer available from DyHydromatics, LLC (Maynard, Mass. USA). A small amount of the coarse emulsion is saved for further analysis.

The high pressure homogenizer is set to 20,000 psi and is equipped with two reaction chambers in series, suitable for emulsions. The reaction chambers are the 75.3 T and the 200.2 L, respectively, which are available from DyHydromatics, LLC. Downstream of the reaction chambers is a coil heat exchanger, which cools the processed material using water at 21° C. as a cooler. The equipment is preheated with hot water to 55-60° C. prior to processing the emulsion. The emulsion is passed three times through the homogenizer at initial temperatures 55, 37, and 30° C. at each pass, respectively. The emulsion is then collected and the particle size analysis is performed.

Particle size analysis is performed using a PSA 1190 L/D Laser Diffraction instrument available from Anton Paar and a Litesizer™ 500 Dynamic Light Scattering instrument also from Anton Paar. The results are shown below.

Coarse Emulsion:
Median Particle size (vol.): 8.44 microns
Final Emulsion:
Hydrodynamic Diameter: 280 nm
Polydispersivity Index: 17.4%

Example 2

Oil/Water Emulsion Using the Method of the Present Disclosure

The formulation by weight and by volume shown in Table 2 is prepared.

TABLE 2

| | Batch Size | |
|---|---|---|
| | 100 g (g) | 100 ml (ml) |
| Mineral oil | 37.00 | 44.58 |
| Tween 80 | 2.40 | |
| Water | 60.60 | 55.42 |

The water (60.60 g) is heated in a beaker on a hot plate to 55° C. Tween® 80 (2.40 g) is added to the water while the mixture is stirred constantly with a magnetic stirrer until the Tween® 80 is completely dissolved. The mineral oil is also heated to 55° C.

A high pressure homogenizer, HP350-30 from DyHydromatics, LLC (Maynard, Mass. USA) is fitted with Delphi Scientific, LLC's dual feed DF-X-01. A 6 inch in-line, static mixer (¼-40-3-12-2) is obtained from Koflo Corporation (Cary, Ill.). A peristaltic pump, Model BT101L-CE Version V122S121 with #15 tubing from Golander, LLC (Norcross, Ga.), is used to pump the oil to the homogenizer at a predetermined rate.

The high pressure homogenizer is set to 20,000 psi and is equipped with two reaction chambers in series, suitable for emulsions. The reaction chambers are the 75.3 T and the 200.2 L, respectively, which are available from DyHydromatics, LLC. Downstream of the reaction chambers is a coil heat exchanger, which cools the processed material using water at 21° C. as a cooler. The homogenizer, dual feed, and all lines are preheated with hot water to 55-60° C. prior to processing.

The flow rate of the homogenizer is first determined under these processing conditions, and such flow rate is measured to be 403 ml/min. Subsequently, the density of the oil is measured at 55° C., and such density is found to be 0.83 g/ml. Therefore, the volume fraction of the oil phase is calculated and shown on Table 2. The flow rate of the oil is then estimated to be 403*44.58/100=179.65 ml/min. The peristaltic pump is set to 179.65 ml/min.

The initial temperatures at each pass through the homogenizer are 55, 37, and 30° C. at each pass, respectively. The emulsion is then collected and the particle size analysis is performed.

Particle size analysis is performed using a PSA 1190 L/D Laser Diffraction instrument available from Anton Paar and a Litesizer™ 500 Dynamic Light Scattering instrument also available from Anton Paar. The results are shown below.

Final Emulsion:
Hydrodynamic Diameter: 241 nm
Polydispersivity Index: 9.6%

Compared to the emulsion of EXAMPLE 1 prepared with the conventional Dual Feed Emulsification Method, the emulsion of EXAMPLE 2 prepared using the method of the present disclosure has smaller particle size (241 nm versus 280 nm), and narrower particle size distribution as inferred by the low Polydispersivity Index (9.6% versus 17.4%).

Examples 3 and 4 compare two different feed systems in terms of accuracy in achieving the desired ratio of the two streams and, therefore, the desired formulation.

Example 3

Propofol emulsion is an emulsion used in anesthesia worldwide. A common formulation of the propofol emulsion shown in Table 3 is prepared.

TABLE 3

| | | Batch size | |
| --- | --- | --- | --- |
| | | 100 g (g) | 100 ml (ml) |
| Oil Phase | Propofol | 1 | |
| | Soybean oil | 5 | |
| | Medium chain triglycerides | 5 | |
| | TOTAL OIL PHASE | 11 | 11.84 |
| Water Phase | Egg Lecithin | 1.2 | |
| | Glycerol | 2.25 | |
| | Sodium Oleate | 0.04 | |
| | WFI | 85.51 | |
| | TOTAL WATER PHASE | 89 | 88.16 |
| | TOTAL FORMULATION | 100 | 100 |

A 400 g batch of propofol emulsion is prepared based on the formulation shown in Table 3 (second column). Water for Injection (WFI) is heated in a beaker on a hot plate to 45° C. Egg lecithin, glycerol, and sodium oleate are added, and the mixture is stirred until all ingredients are dissolved. All ingredients of the oil phase are placed in a beaker and heated to 45° C. The density of the oil and water phases are measured by measuring the weight of a certain volume of each phase. Based on these results, the oil phase is found to be 11.84 vol % and the water phase is found to be 88.16 wt %.

A high pressure homogenizer, HP350-30 from DyHydromatics, LLC (Maynard, Mass. USA) is fitted with Delphi Scientific LLC's dual feed DF-X-01. A 6 inch in-line, static mixer (¼-40-3-12-2) is obtained from Koflo Corporation (Cary, Ill.). A peristaltic pump, Model BT101L-CE Version V122S121 with #15 tubing from Golander, LLC (Norcross, Ga.), is used to pump the oil to the homogenizer at a predetermined rate.

The oil and water phases are then fed separately to a high pressure homogenizer, HP350-30 from DyHydromatics, LLC (Maynard, Mass. USA). The high pressure homogenizer is set to 21,000 psi and is equipped with two reaction chambers in series, suitable for emulsions. The reaction chambers are the 75.3 T and the 200.2 L, respectively, which are available from DyHydromatics, LLC. Downstream of the reaction chambers is a coil heat exchanger, which cools the processed material using water at 21° C. as a cooler. The homogenizer, dual feed, and all lines are preheated with hot water to 45-50° C. prior to processing.

The flow rate of the homogenizer is first determined under these processing conditions, and such flow rate is measured to be 367 ml/min. The flow rate of the oil is then estimated to be 367*11.84/100=40.65 ml/min. The peristaltic pump that feeds the oil phase is set to 43.45 ml/min.

Initially the homogenizer, the inline mixer, and all lines are primed with water to displace the air. Subsequently, the water phase is poured into the reservoir of the homogenizer, while the oil phase is poured into a beaker. The inlet tubing of the peristaltic pump is dipped inside the oil phase and the outlet is connected to one of the ports of the inline mixer. The homogenizer and the peristaltic pump are started. The processed emulsion is collected from the outlet of the homogenizer.

This process is continued until all water and almost all oil is consumed. The amount of the emulsion that is collected and the remaining oil are weighted separately. Based on the amount of oil remaining, the concentration of oil in the emulsion is calculated to be 11.16 wt %, which corresponds to 1.45% higher oil concentration (and therefore drug concentration) of the formulation when compared to the desired 11 wt % oil. These results are within the acceptable range, which is usually +/−2'% from an average value. Additionally, if desired the emulsion may be slightly diluted to achieve the desired 11%.

Example 4

The formulation of Example 3 shown in Table 3 is used in Example 4.

A 400 g batch of the propofol emulsion is prepared based on the formulation shown in Table 3 (second column). Water For Injection (WFI) is heated up in a beaker on a hot plate to 45° C. Egg lecithin, glycerol, and sodium oleate are added and the mixture is stirred until all ingredients are dissolved. All ingredients of the oil phase are placed in a beaker and heated to 45° C. The density of the oil and water phases are measured by measuring the weight of a certain volume of each phase. Based on these results, the oil phase is found to be 11.84 vol % and the water phase 88.16 wt %.

A high pressure homogenizer, HP350-30 from DyHydromatics, LLC (Maynard, Mass. USA) is fitted with a feed system substantially similar to that described in U.S. Pat. Nos. 8,367,004 and 8,187,554, which are assigned to Microfluidics International Corporation, (co-axial feed). A peristaltic pump, Model BT101L-CE Version V122S121 with #15 tubing from Golander, LLC (Norcross, Ga.) is used to pump the water phase. Another peristaltic pump, from LongerPump (Tucson, Ariz.), model YZ1515x with tubing L/S 16 from Masterflex from Cole Palmer (Vernon Hills, Ill.), is used to pump the oil phase. The outlet of each pump is connected to one of the two inlets of a co-axial feed, and such feed consists of two concentric tubes and is positioned at the inlet of the homogenizer. Each liquid stream flows into one tube, and therefore there is no mixing of the two streams until such streams reach the inlet of the homogenizer.

The flow rate of the homogenizer is first determined under these processing conditions, and such flow rate is measured to be 367 ml/min. Subsequently, the density of the oil is measured at 45° C., and such density is found to be 0.92 g/ml. Therefore, the volume fraction of the oil phase is calculated and shown in Table 3. The flow rate of the oil is then estimated to be 367*11.84/100=43.45 ml/min. The peristaltic pump that feeds the oil phase is set to 43.45 ml/min, while the other pump is set to 367−43.45=323.55 ml/min.

Initially the homogenizer, the co-axial feed, and all lines are primed with water to displace the air. Subsequently, the oil and water phases are poured in two separate beakers. The inlet tubing of each peristaltic pump is dipped inside one beaker and the outlet is connected to one of the ports of the co-axial feed. The homogenizer and the peristaltic pumps are started. The processed emulsion is collected from the outlet of the homogenizer.

It is noticed initially that a mostly water phase exited the homogenizer, which is easy to determine because the water phase is light yellow and fairly translucent while the processed emulsion is opaque and white in color. The water phase is discarded. Eventually, the white emulsion began to exit the homogenizer. The white emulsion is collected in a beaker.

This process is continued until almost all oil and water phases are consumed. The amount of the emulsion that is collected and the remaining oil and water phases are weighed separately. Based on the amount of oil and water phases remaining, the concentration of oil in the emulsion is calculated to be 9.97 wt %, which corresponds to 9.34% error in oil concentration (and therefore the drug concentration) of the formulation when compared to the desired 11 wt % oil. The formulation prepared in this EXAMPLE 4 is outside of the acceptable range, and such formulation cannot be diluted further to achieve the acceptable specifications.

Example 5

The formulation Example 2 shown in Table 2 is used in the system described in EXAMPLE 4. The set point of the flow rate of the oil pump is increased by 9.34% to 47.54 ml/min (by 4.09 ml/min) while the flow rate of the water is decreased by the same amount (4.09 ml/min), which would simulate automatic control of the pump flow rates.

After the experiment, the oil content is inferred, and such oil content is found to be 9.97 wt %. The oil content is again lower than the desirable by 9.36%, which is unacceptable in most applications.

Example 6

Norfloxacin (NFN), which is a highly hydrophobic (having limited solubility in water) pharmaceutical, is selected as a model drug to demonstrate the applicability of the disclosed apparatus, systems and methods based on: (a) limited water solubility, (b) availability, and (c) price. Norfloxacin is recrystallized using the method of the present disclosure to obtain submicron particles. Such particles may increase the bioavailability of norfloxacin, which such bioavailability is limited by norfloxacin's limited water solubility.

10 mg of norfloxacin is dissolved completely in 40 g of dimethyl sulfoxide (DMSO) at about 30° C. and is mixed using a magnetic stirrer. About 160 ml of water is mixed with 2 grams of surfactant Tween® 80. When the stream of norfloxacin dissolved in DMSO mixes with the stream of water mixed with Tween® 80, the norfloxacin is not soluble in the mixture of the DMSO, water, and Tween® 80. Therefore, the norfloxacin crystallizes.

The system described in Example 2 is used for processing. The total flow rate of the equipment is 403 ml/min. The density of the DMSO phase is determined to be 1.1 g/ml. The desired volume fraction of the DMSO phase compared to the total volume flow rate of the machine is 18.48%. The total flow rate of the peristaltic pump that delivers the DMSO phase is set to 74.48 ml/min.

The two streams are processed once through the equipment to ensure mixing and interaction of the full amount of the DMSO phase with the water phase. A liquid dispersion containing white norfloxacin particles is obtained, and such dispersion is then again passed through the homogenizer. This time the port that delivered the DMSO mixture is not used and is closed. The dispersion is poured into the machine reservoir and is delivered to the homogenizer as a single mixture. The dispersion is processed again to de-agglomerate possible agglomerates formed during the first pass.

Particle size of the material is conducted using a Litesizer Dynamic Light Scattering instrument available from Anton Paar. The average particle size is found to be 154 nm.

Although the present disclosure has been described with reference to exemplary embodiments and implementations thereof, the present disclosure is not limited by such illustrative embodiments/implementations. Rather, the present disclosure is subject to changes, modifications, enhancements and/or variations with departing from the spirit or scope hereof. Indeed, the present disclosure expressly encompasses all such changes, modifications, enhancements and variations within its scope.

What is claimed is:

1. A method for continuously processing at least two liquid feed streams, comprising:
    pumping a first feed stream to an in-line mixer at an actively automatically controlled rate;
    flowing a second feed stream to the in-line mixer;
    mixing the first and second feed streams to achieve a substantially homogeneous mixture;
    pumping the substantially homogeneous mixture to a high pressure pump at an actively controlled rate;
    pressurizing the substantially homogeneous mixture within the high pressure pump to an elevated pressure of at least 35 MPa; and
    delivering the substantially homogeneous mixture to a microreactor downstream from the high pressure pump, the microreactor having a minimum channel dimension of equal to or less than 500 microns, causing the first and second liquid streams to interact within the microreactor at a nanoscale level,
    wherein mixing the first and second feed streams to achieve the substantially homogenous mixture includes mixing the first and second feed streams with the in-line mixer at a location that is upstream of the high pressure pump and upstream of a component arranged between the in-line mixer and the high pressure pump.

2. The method of claim 1, wherein the first feed stream includes a first constituent, and wherein the second feed stream includes a second constituent.

3. The method of claim 1, wherein the first and second feed streams are delivered to the in-line mixer in feed lines that are coaxially aligned.

4. The method of claim 1, wherein the first and second feed streams are introduced to the in-line mixer through spaced ports defined by the in-line mixer.

5. The method of claim 1, wherein the actively controlled rate for delivery of the first feed stream to the in-line mixer is effected by an actively controlled feed pump for the first feed stream.

6. The method of claim 1, further comprising cooling or quenching the substantially homogenous mixture after interaction within the microreactor.

7. The method of claim 2, wherein the first constituent includes a solvent, and wherein the second constituent includes an antisolvent, and wherein interaction of the solvent and the antisolvent in the microreactor is effective to define a nanosuspension, the method further comprising:
obtaining constituent nanoparticle crystals from the nanosuspension.

8. The method of claim 7, wherein the solvent stream is selected from the group consisting of dimethyl sulfoxide (DMSO), N-Methyl-2-Purrolidone (NMP), methanol, ethanol, acetone, dichloromethane, octanol and isopropyl alcohol, and the antisolvent stream is selected from the group consisting of water, hexane and heptane.

9. The method of claim 8, wherein the solvent stream is DMSO and nanoparticles of azithromycin are obtained at a median particle size of about 50-100 nm.

10. The method of claim 8, wherein the solvent stream is DMSO and nanoparticles of oxycarbazepine are obtained at a median particle size less than 1000 nm.

11. The method of claim 8, wherein the solvent stream is DMSO or NMP and nanoparticles of loratadine are obtained at a median particle size of less than 500 nm.

12. The method of claim 7, further comprising cooling or quenching the nanosuspension after interaction within the microreactor.

13. The method of claim 1, wherein the elevated pressure is at least about 70 MPa.

14. The method of claim 1, wherein the elevated pressure is at least about 140 MPa.

15. The method of claim 1, wherein the elevated pressure is at least about 207 MPa.

16. The method of claim 1, wherein the ratio of the flow rate of the second stream to the flow rate of the first stream is at least about 2:1.

17. The method of claim 1, wherein the ratio of the flow rate of the second stream to the flow rate of the first stream is at least about 3:1.

18. The system of claim 1, wherein the ratio of the flow rate of the second stream to the flow rate of the first stream is at least about 10:1.

19. The method of claim 1, wherein the microreactor has channels with minimum dimensions in the range of 10-500 microns.

20. The method of claim 1, wherein the average fluid velocity in microreactor channels is in the range of 300-500 m/s.

21. The method of claim 1, further comprising effecting a sheer rate in the microreactor of at least about $1.2 \times 10^6$ s$^{-1}$.

22. The method of claim 1, wherein the microreactor has a single slot geometry.

23. The method of claim 1, wherein at least one of the liquid feed streams includes solid particles.

24. The method of claim 7, wherein at least one of the feed streams contains seed particles.

25. The method of claim 7, wherein at least one of the feed streams contains catalyst particles.

26. The method of claim 2, wherein the first constituent is a first reactant and the second constituent is a second reactant, the method further comprising:
adjusting reaction selectivity by controlling interaction between the first and second reactants prior to the nanoscale level interaction within the microreactor.

27. The method of claim 26, wherein control of the interaction between the first and second reactants is effected by encouraging contact between the first and second reactants in the in-line mixer prior to pressurization in the high pressure pump so as to achieve the substantially homogeneous mixture.

28. The method of claim 26, wherein the substantially homogeneous mixture is pumped to the high pressure pump through a port defined by the high pressure pump.

29. The method of claim 28, further comprising cooling or quenching the substantially homogeneous mixture after reaction within the microreactor.

30. The method of claim 1, wherein the first and second feed streams are immiscible.

31. The method of claim 1, wherein the first and second feed streams are miscible.

32. The method of claim 2, wherein the constituents interact within the microreactor to achieve an emulsion, a dispersion, a liposomal formulation, lipid nanoparticles, or a crystalline or amorphous material.

33. The method of claim 1, wherein the first feed stream is an oil phase and the second feed stream is a water phase.

34. The method of claim 33, wherein the oil phase is selected from a vegetable oil, a nut oil, an animal oil, an inorganic oil, a lipid, a surfactant, a polymer, an active ingredient, a flavoring, a coloring, an alcohol, an organic solvent, and/or a derivative thereof.

35. The method of claim 33, wherein the water phase is selected from a water, a lipid, a surfactant, a viscosity modifier, a pH adjuster, and a sugar.

36. The method of claim 1, wherein the first feed stream is a water phase and the second feed stream is an oil phase.

37. The method of claim 36, wherein the oil phase is selected from a vegetable oil, a nut oil, an animal oil, an inorganic oil, a lipid, a surfactant, a polymer, an active ingredient, a flavoring, a coloring, an alcohol, an organic solvent, and/or a derivative thereof.

38. The method of claim 36, wherein the water phase is selected from a water, a lipid, a surfactant, a viscosity modifier, a pH adjuster, and a sugar.

39. The method of claim 1, wherein the component is selected from one of the following: a conduit, an overflow tank, a pressurized tank, a check valve, a flow control valve, a mixing valve, a solenoid valve, a feed pump, a peristaltic pump, a centrifugal pump, a filter, a screen, a temperature sensor, a pressure sensor, a sampling port, or a metering pump.

40. A system for continuously processing at least two liquid feed streams, comprising:
a feed pump that is adapted to pump a first feed stream downstream at an actively automatically controlled rate;
an in-line mixer positioned to receive the first feed stream from the feed pump and a second feed stream from a feed line, the in-line mixer adapted to mix the first and second feed streams to achieve a substantially homogeneous mixture;

a high pressure pump positioned to receive the substantially homogeneous mixture from the in-line mixture, the high pressure pump adapted to pressurize the first and second feed streams to an elevated pressure of at least 35 MPa; and a microreactor downstream of the high pressure pump, the microreactor having a minimum channel dimension of equal to or less than 500 microns, the microreactor adapted to effect high shear fields so as to achieve thorough mixing of the substantially homogeneous mixture, wherein the in-line mixer is located upstream of the high pressure pump and upstream of a component arranged between the in-line mixer and the high pressure pump.

41. The system of claim 40, wherein the feed pump is a metering pump.

42. The system of claim 40, wherein the first and second feed streams are delivered to the in-line mixer in a coaxial arrangement.

43. The system of claim 40, wherein the microreactor has a single slot geometry.

44. The system of claim 40, further comprising a cooling unit downstream of the microreactor.

45. The system of claim 40, wherein the in-line mixer includes a plurality of spaced feed ports, and wherein the first feed stream is introduced to the in-line mixer through a first feed port and the second feed stream is introduced to the in-line mixer through a second feed port.

46. The system of claim 40, wherein the first feed stream includes a first constituent, and wherein the second feed stream includes a second constituent and wherein the microreactor is adapted to effect a controlled nanoscale interaction between the first constituent and the second constituent.

47. The system of claim 40, wherein the microreactor is adapted to effect interaction of a first reactant in the first feed stream and a second reactant in the second feed stream at a nanoscale level, and the system is configured so that reaction selectivity can be controlled by controlling interaction between the first and second reactants prior to the nanoscale level interaction within the microreactor.

48. The system of claim 47, wherein control of the interaction between the first and second reactants is effected by encouraging contact between the first and second reactants in the in-line mixer prior to pressurization in the high pressure pump so as to achieve the substantially homogeneous mixture.

49. The system of claim 47, wherein the first and second reactants are delivered to the in-line mixer through spaced ports defined by the in-line mixer.

50. The system of claim 40, wherein the elevated pressure is at least about 70 Mpa.

51. The system of claim 40, wherein the elevated pressure is at least about 140 MPa.

52. The system of claim 40, wherein the elevated pressure is at least about 207 MPa.

53. The system of claim 40, wherein the ratio of the flow rate of the second stream to the flow rate of the first stream is at least about 2:1.

54. The system of claim 40, wherein the ratio of the flow rate of the second stream to the flow rate of the first stream is at least about 3:1.

55. The system of claim 40, wherein the ratio of the flow rate of the second stream to the flow rate of the first stream is at least about 10:1.

56. The system of claim 40, wherein the microreactor has channels with minimum dimensions in the range of 10-500 microns.

57. The system of claim 40, wherein the average fluid velocity in microreactor channels is in the range of 300-500 m/s.

58. The system of claim 40, wherein the sheer rate effected in the microreactor is at least about $1.2 \times 10^6$ $s^{-1}$.

59. The system of claim 40, wherein the microreactor has a single geometry.

* * * * *